(12) United States Patent
Fischer et al.

(10) Patent No.: US 6,527,751 B2
(45) Date of Patent: Mar. 4, 2003

(54) HYDRAULIC SYRINGE AND METHOD OF MANUFACTURE

(75) Inventors: Dan E. Fischer, Sandy, UT (US); David V. Fischer, Colton, CA (US); Bruce S. McLean, Sandy, UT (US); Samuel A. Howard, Magna, UT (US); Andrew Wight, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/742,516

(22) Filed: Dec. 20, 2000

(65) Prior Publication Data

US 2001/0021828 A1 Sep. 13, 2001

Related U.S. Application Data

(63) Continuation-in-part of application No. 09/467,419, filed on Dec. 20, 1999.

(51) Int. Cl.[7] .............................................. A61M 5/315
(52) U.S. Cl. ...................................... 604/218; 604/187
(58) Field of Search ................................. 604/218, 221, 604/222, 228, 229, 230, 232, 187, 207, 208

(56) References Cited

U.S. PATENT DOCUMENTS

| 4,065,230 A | | 12/1977 | Gezari ........................ 417/317 |
| 4,177,810 A | | 12/1979 | Gourlandt ................... 128/218 |
| 4,295,828 A | | 10/1981 | Rudler ......................... 433/90 |
| 4,323,066 A | * | 4/1982 | Bourdon ..................... 128/218 |
| 4,327,724 A | | 5/1982 | Birk et al. .................. 128/218 |
| 4,330,280 A | | 5/1982 | Dougherty et al. ........... 433/90 |
| 4,348,160 A | | 9/1982 | Heyneman ................... 417/403 |
| 4,384,853 A | | 5/1983 | Welsh ........................... 433/90 |
| 4,391,590 A | | 7/1983 | Dougherty ................... 433/90 |
| 4,767,326 A | | 8/1988 | Bennett et al. ................ 433/90 |
| 4,878,601 A | | 11/1989 | Flemming et al. .......... 222/137 |
| 5,058,779 A | | 10/1991 | Surdilla ...................... 222/309 |
| 5,203,839 A | | 4/1993 | Skaggs ....................... 222/137 |
| 5,259,842 A | | 11/1993 | Plechinger et al. ......... 604/152 |
| 5,286,257 A | | 2/1994 | Fischer ......................... 604/82 |
| 5,458,275 A | | 10/1995 | Centea et al. ............... 222/309 |
| 5,529,463 A | | 6/1996 | Layer et al. ................ 417/403 |
| 5,626,473 A | | 5/1997 | Muhlbauer et al. ........... 433/89 |
| 5,707,234 A | | 1/1998 | Bender ......................... 433/90 |
| 5,782,633 A | | 7/1998 | Muhlbauer .................... 433/90 |
| 6,280,421 B1 | * | 8/2001 | Kirchhofer et al. ......... 604/218 |

* cited by examiner

Primary Examiner—Anhtuan T. Nguyen
Assistant Examiner—Ann Y Lam
(74) Attorney, Agent, or Firm—Workman, Nydegger & Seeley

(57) ABSTRACT

A manually operated hydraulic syringe includes a syringe barrel. The syringe barrel has an interior surface bounding a chamber extending from a first end to an opposing second end. A manual plunger has a distal end slidably disposed within the first end of the chamber. A hydraulic plunger is slidably enclosed within the second end of the chamber. Sealed in substantial isolation within the syringe barrel is a hydraulic fluid, such as water or oil. Coupled to the distal end of the syringe barrel is a nozzle or cartridge in which a dispensing material, such as a high viscosity fluid, can be selectively disposed. Manual advancement of the manual plunger within the first chamber results in pressurization of the hydraulic fluid. In turn, the pressurized hydraulic fluid advances the hydraulic plunger under a force greater than the force applied to the manual plunger. Advancement of the hydraulic plunger within the syringe body functions to dispense the dispensing material from the attached nozzle or cartridge.

30 Claims, 15 Drawing Sheets

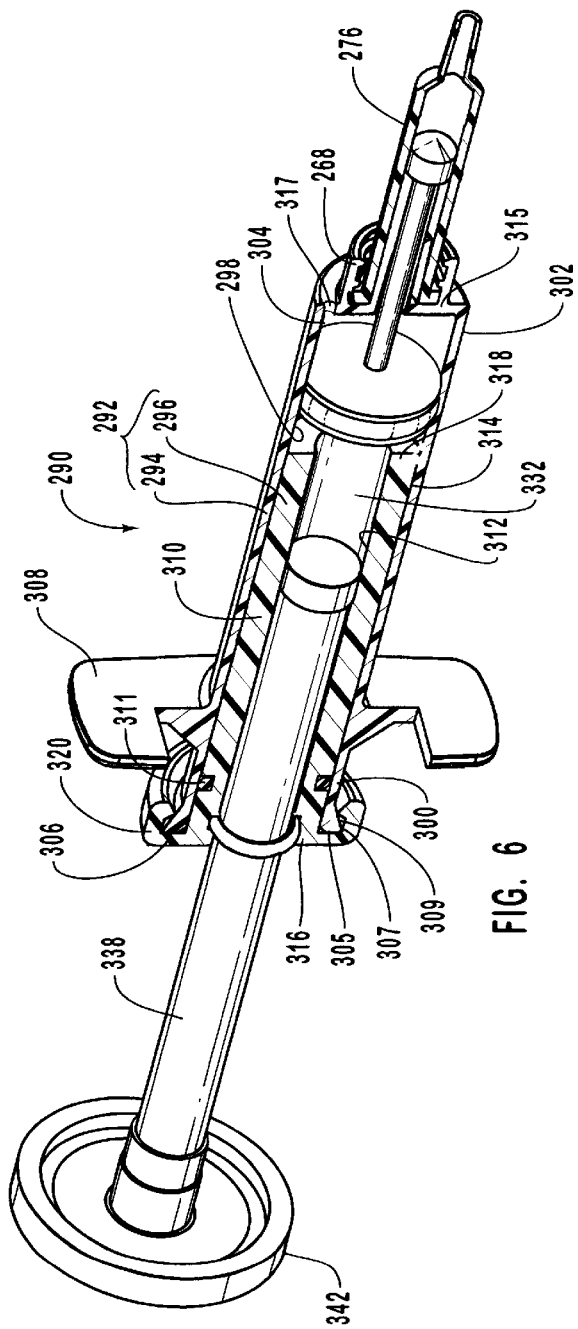
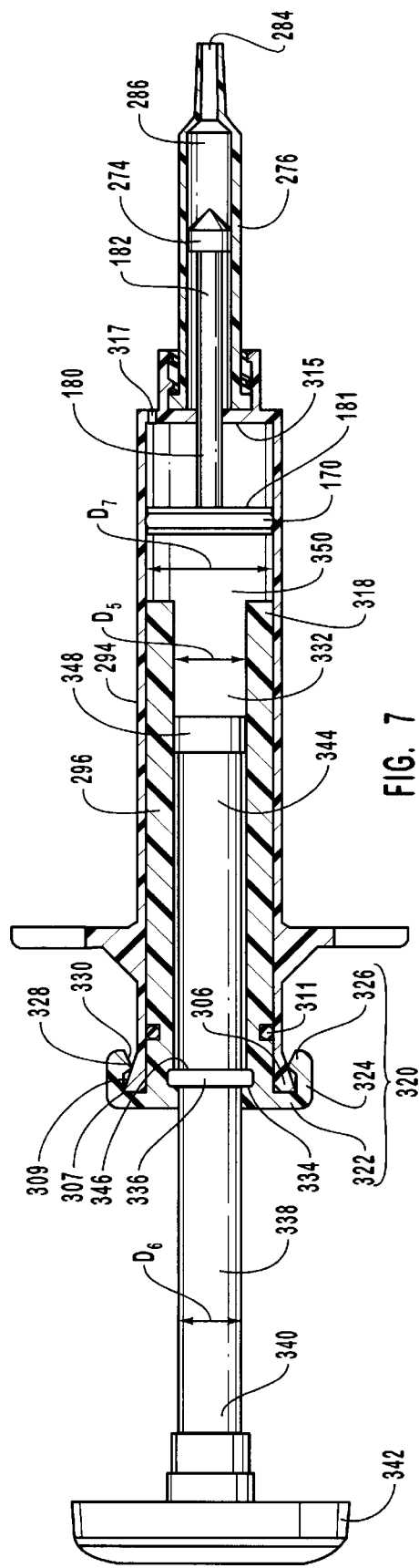
FIG. 6
FIG. 7

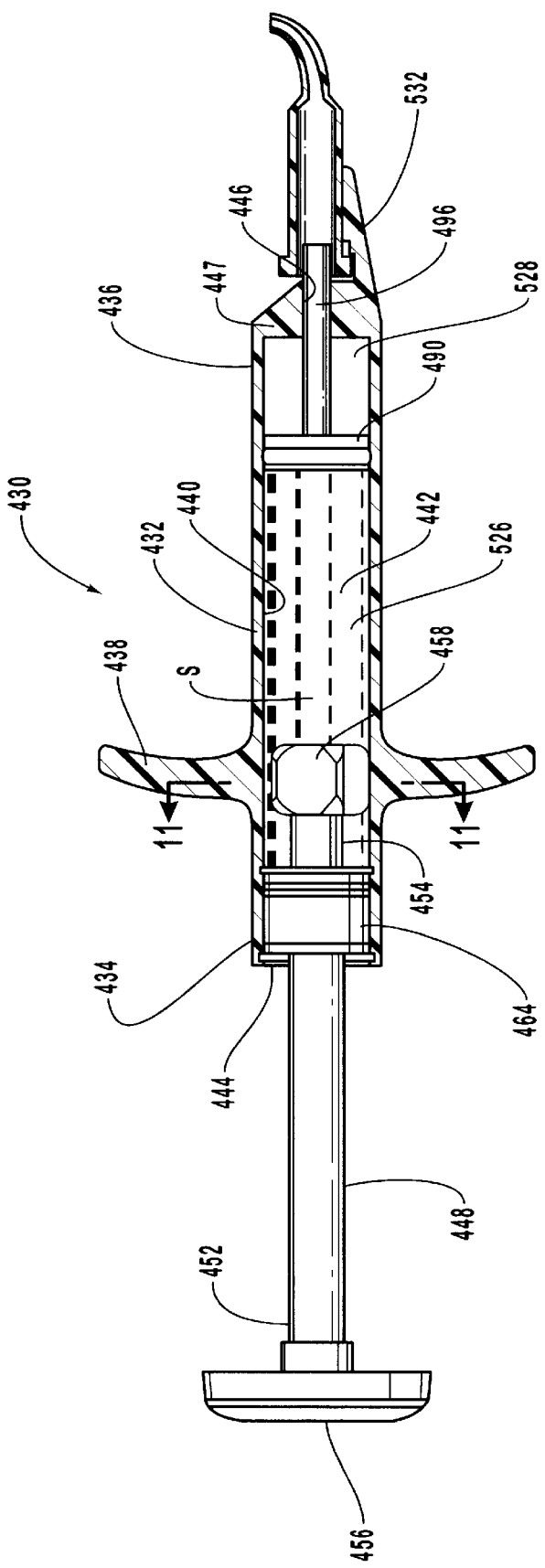
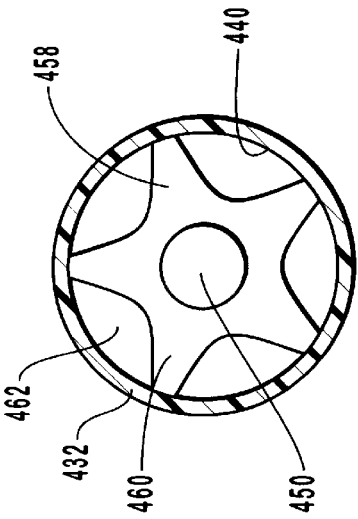
FIG. 10
FIG. 11

HYDRAULIC SYRINGE AND METHOD OF MANUFACTURE

This application is a continuation in part of U.S. patent application Ser. No. 09/467,419, filed Dec. 20, 1999, which for purposes of disclosure is incorporated herein by specific reference.

BACKGROUND OF THE INVENTION

1. The Field of the Invention

The present invention relates to syringes. Specifically, the present invention relates to manually operated hydraulic syringes and methods of manufacture.

2. Prior State of the Art

Syringes are widely used to inject, dispense and extract fluids in a controlled fashion. Conventional syringes generally consist of a syringe body having a cylindrical chamber in which a piston is forced to slide. The chamber has an orifice in the end opposite the piston such that if the piston is pushed towards the orifice, fluid is ejected from the chamber into or onto a target. If the piston is forced away from the orifice, fluid at the orifice is vacuumed into the chamber.

As apparent, a source of force is needed to operate a syringe. A non-human driving mechanism, such as an electrical motor, provides this force in automated syringes. Many syringes, however, operate under the manual force of a user. Although typically less sophisticated than automated syringes, manual syringes are widely used because they are inexpensive, easily maneuverable, disposable, and do not require complex and bulky driving mechanisms.

Syringes are often used in dispensing high viscosity fluids. For example, in dentistry, high viscosity fluids such as uncured dental filling materials are often dispensed onto small targets such as a pre-drilled tooth cavity. Dispensing high viscosity fluids, however, requires the user to exert a relatively high force on the manual syringe. This required exertion can produce undesired stress and fatigue on the user. Furthermore, dispensing high viscosity fluids can be more difficult to control. For example, because of the high exertion force required to dispense high viscosity materials, it can be difficult to dispense small controlled amounts or to dispense the material at a constant or desired flow rate. The high exertion force can also result in the operator's hand becoming shaky or unstable. Such shaking and lack of control can result in the fluid missing the target.

In one approach to overcome some of the above problems, devices such as caulking type guns have been used to dispense high viscosity fluids. Caulking type guns have a levered handle which produces a mechanical advantage. Such devices, however, are large and cumbersome relative to conventional syringes. Furthermore, some caulking type guns operate on a ratcheting system which makes it difficult to dispense in a smooth, continuous manner. Finally, since caulking type guns have a handle that orthogonally projects from the barrel, caulking type guns are limited in their use and maneuverability Therefore, an easily maneuverable apparatus and method are desired for the controlled manual dispensing of high viscosity fluids.

BRIEF SUMMARY OF THE INVENTION

A hydraulic syringe includes a syringe barrel having an exterior surface and an interior surface. A syringe grip outwardly projects from the exterior surface of the syringe barrel. The interior surface of the syringe barrel bounds a chamber having a substantially uniform transverse cross sectional area along its length. Sealed within the chamber is a hydraulic fluid. A manual plunger is coupled with the first end of the barrel so as to selectively advance within the chamber thereof. A hydraulic plunger is slidably disposed within the second end of the barrel. As the manual plunger is advanced, the hydraulic fluid is pressurized which in turn causes the hydraulic plunger to advance.

One of the unique features of the present invention is that the manual plunger has a transverse cross sectional area that is smaller than the maximum transverse cross sectional area of the hydraulic plunger. As a result, a hydraulic advantage is achieved. That is, as the manual plunger is advanced within the chamber under a first force at a first speed, the hydraulic fluid is pressurized. In turn, the pressurized hydraulic fluid pushes against the hydraulic plunger. As a result of the hydraulic plunger having a larger surface area of displacement, the hydraulic plunger moves forward with a second force that is greater than the first force and at a second speed that is slower than the first speed. In turn, this magnified or increased second force is applied through the hydraulic plunger to the high viscosity fluid for dispensing.

Once the material has been dispensed by the hydraulic syringe, a spring disposed between the hydraulic plunger and the second end of the barrel is used to help retract the hydraulic plunger. Furthermore, one or more retraction rods are secured to the hydraulic plunger so as to project towards the first end of the syringe barrel. A guide is mounted on and radially outwardly projects from the manual plunger. Each rod extends through a passageway formed on the guide such that the guide can freely slide along the length of each rod. However, the rods are also formed such that as the manual plunger is retracted, the guide secures to the end of each rod resulting in both the rods and the hydraulic plunger being retracted as the manual plunger is retracted.

In the above embodiment, as a result of the magnification of force, minimal manual force is required to be applied by the user of the hydraulic syringe to effectively dispense high viscosity fluids in a controlled manner. Furthermore, since minimal force and thus minimal exertion is required by the user, fatigue and shaking by the user is also minimized. Finally, since the hydraulic syringe has a configuration similar to a conventional syringe, the hydraulic syringe is convenient and easily maneuvered by the user. That is, rotation of the wrist facilitates quick and easy placement for most delivery angles.

These and other features and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6 is a partial cross section isometric view of an alternative embodiment of a hydraulic syringe having an inner barrel and outer barrel;

FIG. 7 is a partial cross sectional side view of the hydraulic syringe shown in FIG. 6;

FIG. 8 is a cross sectional side view of an alternative embodiment of a hydraulic syringe wherein the manual plunger has a channel longitudinally extending there through;

FIG. 10 is a cross sectional side view of another alternative embodiment of a hydraulic syringe;

FIG. 11 is a cross sectional side view of the guide shown in FIG. 10 taken along section lines 11—11;

DETAILED DESCRIPTION OF THE PREFERRED EMBODIMENTS

Figure 1:
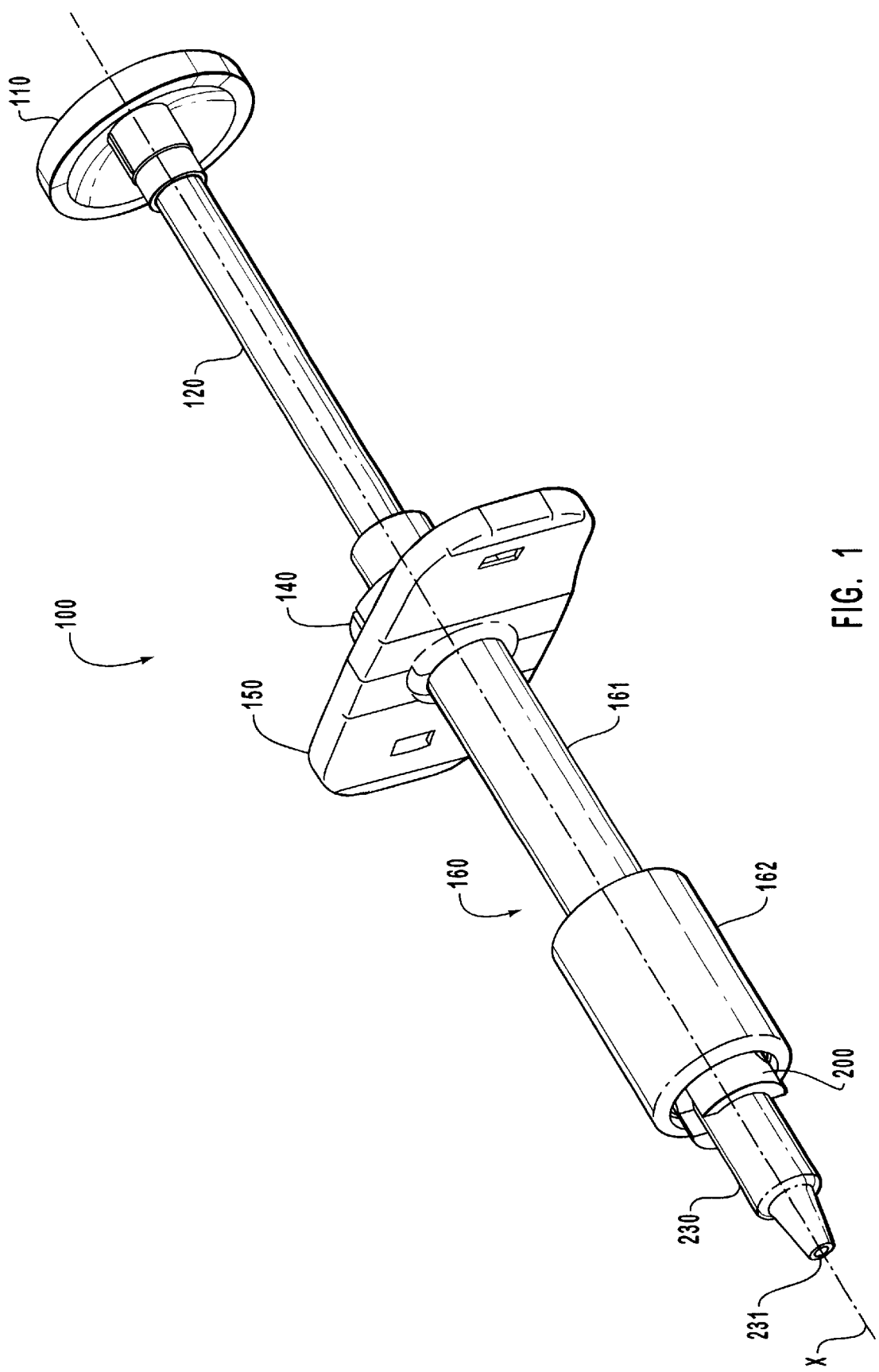
FIG. 1 is an isometric view of one embodiment of a hydraulic syringe.

Referring to FIG. 1, a syringe 100 is manually operated by squeezing a handle 110 towards a grip 150. This manual force is hydraulically converted within syringe 100 into an increased force which urges working material from a nozzle 230 out through an orifice 231 thereof. In the description and claims, "hydraulically" is defined as "of, involving, moved, or operated by pressurized fluid including any fluid in the liquid or gaseous phases." As a result of producing an increased force from an initial manual force, the inventive syringe can be used to more easily dispense highly viscous materials.

The term "syringe" as used in the specification and appended claims is broadly intended to include all types of dispensing apparatus which include a hollow barrel and a plunger. The inventive syringes can be used for medical uses and non-medial uses, such as industrial and home use. Furthermore, although the inventive syringes are depicted herein as having a configuration similar to a conventional medical syringe, the inventive syringe may also have the configuration of a caulking gun or other apparatus used in dispensing material.

The structural and operational details of syringe 100 are now described with reference to FIG. 2 which shows syringe 100 in an exploded view, and FIG. 3 which shows a portion of syringe 100 in cross-section. The structure of syringe 100 will be described in order beginning with handle 110 at the upper right corner of FIGS. 2 and 3 and proceeding diagonally downwards and to the left, finishing with nozzle 230 at the lower left corner of FIGS. 2 and 3.

Figure 2:
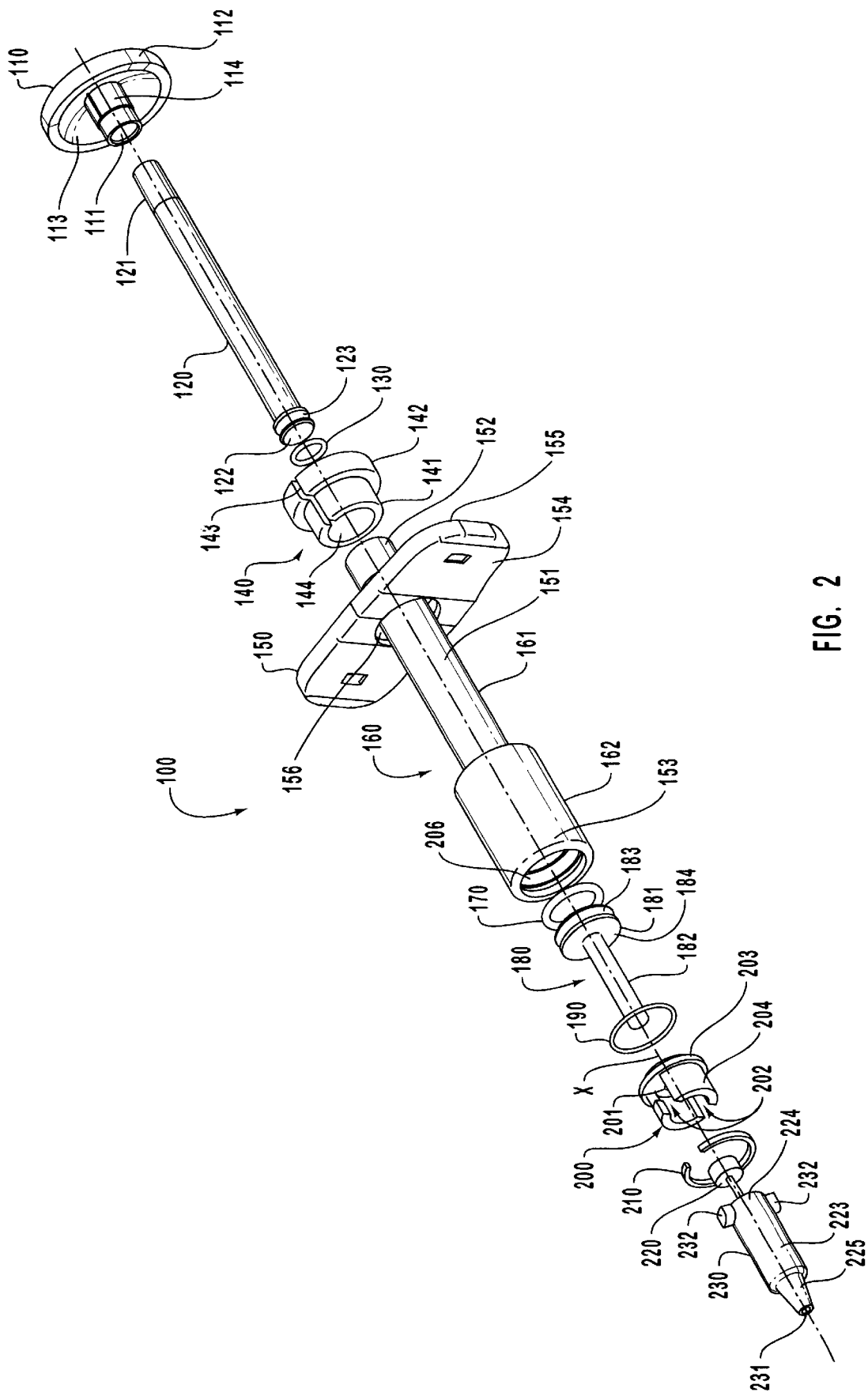
FIG. 2 is an exploded isometric view of the syringe of FIG. 1.

As depicted in FIG. 2, handle 110 includes an enlarged annular rest 112 having a front face 113. Projecting from front face 113 is a tubular stem 114. Stem 114 bounds a cylindrical hole 111.

An elongated manual plunger 120 has a proximate end 121 and an opposing distal end 122. In this description and in the claims, "distal" means towards the lower left corner of FIGS. 1–3 and "proximate" means towards the upper right corner of FIGS. 1–3. Proximate end 121 of manual plunger 120 is attached to handle 110 by being inserted within cylindrical hole 111. In an alternative embodiment, handle 110 can be integrally molded with manual plunger 120. In yet other embodiments, handle 110 and manual plunger 120 can be mechanically, chemically, or otherwise secured together. Encircling distal end 122 of manual plunger 120 is an annular groove 123. Groove 123 is configured to receive a flexible seal 130. Seal 130 and other seals set forth in the specification and appended claims are broadly intended to include o-rings, loaded lip seals, including those with bevel lips, packing material, gaskets, and any other conventional type of seal or sealing material. Examples of loaded lip seals include Standard PolyPak, Deep PolyPak, and Pip Seals available from Parker Seals out of Irving, Calif.

Proceeding diagonally downwards and to the left, a tubular grip retainer 140 bounds a passageway 144 extending there through. Grip retainer 140 includes a first collar portion 141 having a first outer diameter and a second collar portion 142 concentrically aligned with first collar portion 141. Second collar portion 142 has a second outer diameter larger than the first outer diameter. A slot 143 longitudinally extends along the length of grip retainer 140. Slot 143 enables grip retainer 140 to selectively radially expand and constrict. An elongated grip 150 has a front face 154, an opposing back face 155, and an aperture 156 centrally extending therebetween. Grip retainer 140 is used to secure grip 150 to a syringe barrel 160. Specifically, syringe barrel 160 has an elongated tubular configuration with an exterior surface 151 that longitudinally extends between a proximate end 152 and an opposing distal end 153. As depicted in FIG. 3, an annular lip 158 radially outwardly projects from exterior surface 151 at proximate end 152.

During assembly, as depicted in FIG. 2, proximate end 152 of syringe barrel 160 is received through aperture 156 of grip 150 so that grip 150 is distal of lip 158. Next, proximate end 152 of syringe barrel 160 is received through passageway 144 of grip retainer 140 so that second collar portion 142 of grip retainer 140 is distal of lip 158. Grip 150 is then slid proximal such that first collar portion 141 of grip retainer 140 is received within the remainder of aperture 156 extending between syringe barrel 160 and grip 150. Aperture 156 is configured such that as first collar portion 141 is received within aperture 156, grip retainer 140 is constricted by the closure of slot 143. The closure of slot 143 results in grip retainer 140 biasing in frictional engagement against exterior surface 151 of syringe barrel 160. In this constricted position, grip retainer 140 is also biased against lip 158 which acts as a stop to prevent grip retainer 140 from sliding proximal. In turn, grip 150 is biased against second collar portion 142 which acts as a stop to preclude grip 150 from further sliding proximal. In alternative embodiments, grip 150 can be secured by alternative means such as adhesion or mechanical locking. In yet other embodiments, grip 150 can be integrally molded with syringe barrel 160.

Returning to FIG. 3, syringe barrel 160 includes a first tubular portion 161 and an adjacent second tubular portion 162. First tubular portion 161 has an interior surface 163 that bounds a first chamber 164 and longitudinally extends from proximal end 152 to a distal end 166. In the embodiment depicted, first chamber 164 has a substantially cylindrical transverse cross sectional area with a diameter $D_1$. In this description and in the claims, "transverse" means in a plane perpendicular to the longitudinal axis (X) of syringe 100.

Distal end 122 of manual plunger 120 is configured to be received within first chamber 164 such that distal end 122 is slidable therein along the range (Q). Furthermore, manual plunger 120 is configured such that seal 130 biases against interior surface 163 bounding first chamber 164 so as to effect a liquid tight seal as manual plunger 120 is advanced and retracted within first chamber 164. In yet other embodiments, seal 130 can be replaced with a rubber bulb or other means for effecting a liquid tight seal between manual plunger 120 and interior surface 163 as manual plunger 120 is advanced and retracted within first chamber 164.

Second tubular portion 162 of syringe barrel 160 includes an interior surface 167 bounding a second chamber 165. Second chamber 165 longitudinally extends from a proximal end 168 to distal end 153. In the embodiment depicted, second chamber 165 has a substantially cylindrical transverse cross sectional area with a diameter $D_2$. Diameter $D_2$ is larger than diameter $D_1$. As such, the transverse cross sectional area of second chamber 165 is larger than the transverse cross sectional area of first chamber 164. Second tubular portion 162 is concentrically coupled with first tubular portion 161 such that first chamber 164 is fluid coupled with second chamber 165.

Slidably disposed within second chamber 165 is a hydraulic plunger 180. In the embodiment depicted, hydraulic plunger 180 includes a cylindrical head 181 having a perimeter groove 183 configured to receive an annular seal 170. Projecting from a front face 184 of head 181 is a shaft 182. Hydraulic plunger 180 is configured such that when received within second chamber 165, seal 170 biases against interior surface 167 so as to effect a liquid tight seal as hydraulic plunger 180 advances and retracts within second chamber 165 along range (q).

Figure 3:
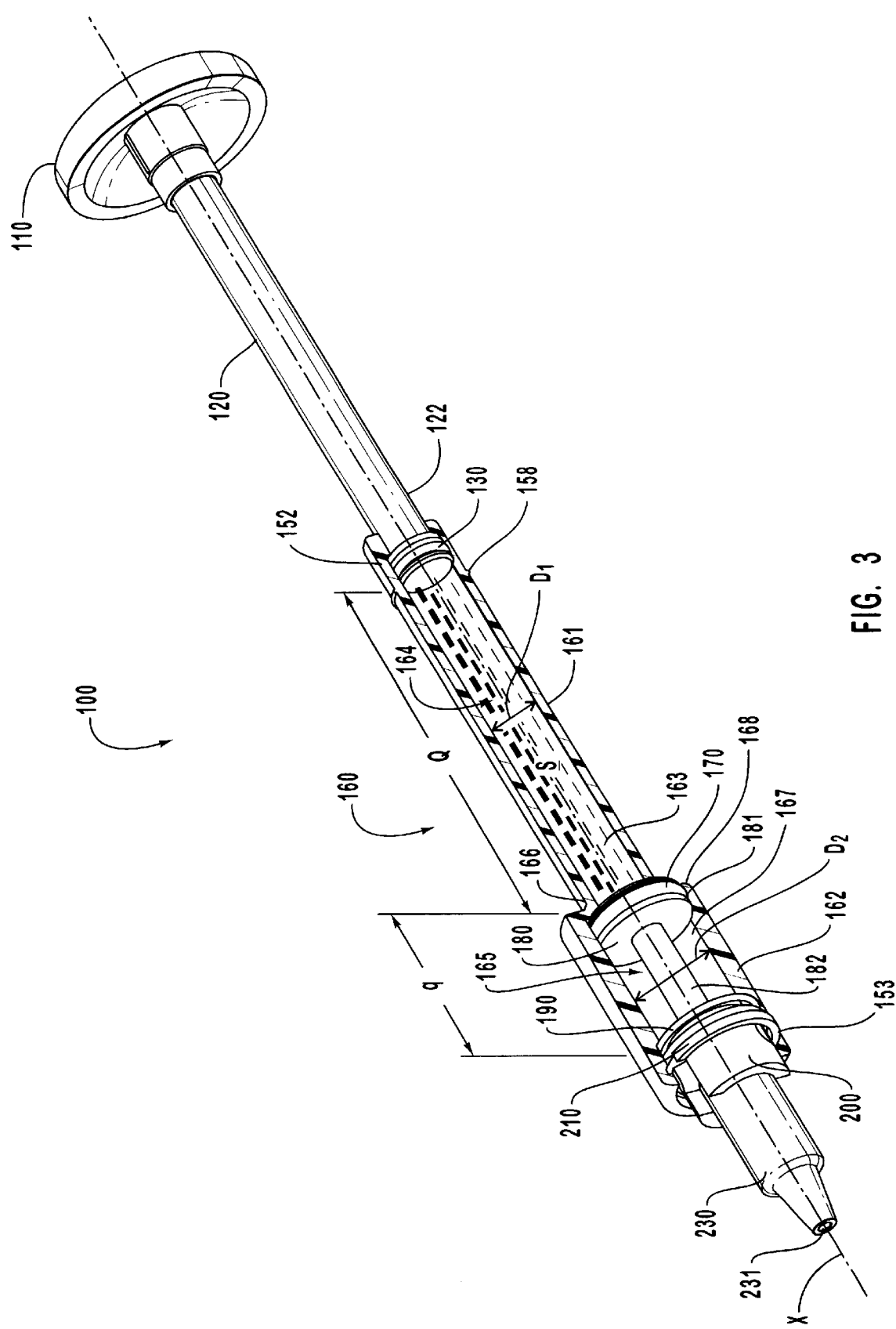
FIG. 3 is an isometric view of the syringe of FIG. 1 with the syringe barrel viewed in cross section and with the grip removed to show the hydraulic advantage of the syringe.

Prior to use, as depicted in FIG. 3, a hydraulic fluid (S), such as water, a saline solution, oil, or a gas, is sealed within syringe barrel 160 between distal end 122 of manual plunger 120 and head 181 of hydraulic plunger 180. One example of a hydraulic fluid is polydimethyal siloxane having a viscosity in a range between about 10 centistoke to about 100,000 centistoke, with about 500 centistoke to about 5,000 centistoke being more preferred.

In one method for incorporating hydraulic fluid (S), distal end 122 of manual plunger 120 is slidably moved to the most distal end of range (Q). Hydraulic fluid (S) is then poured into second chamber 165 through open distal end 153 of syringe barrel 160 so as to substantially fill second chamber 165. Next, hydraulic plunger 180 is inserted within distal end 153 of syringe barrel 160 so as to effectively seal off hydraulic fluid (S) from the ambient environment. Accordingly, as manual plunger 120 is withdrawn within first chamber 164, hydraulic fluid (S) flows into first chamber 164 while hydraulic plunger 180 advances within second chamber 165 under the vacuum force produced by manual plunger 120.

Figure 4:
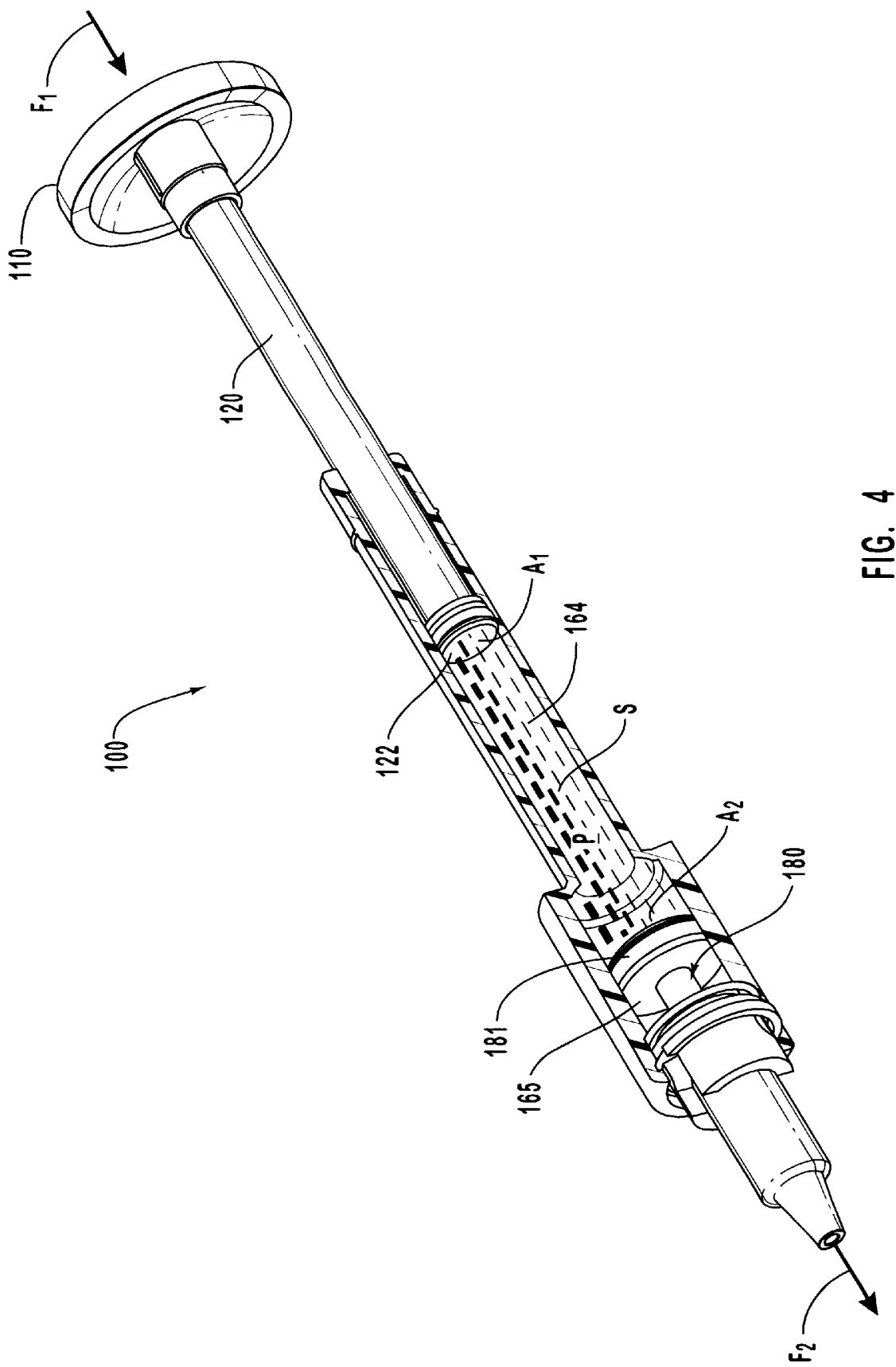
FIG. 4 is an isometric view of the syringe of FIG. 3 wherein the plungers are advanced under a force.

As depicted in FIG. 4, during use an operator manually applies a force ($F_1$) to handle 110 so that distal end 122 of the manual plunger 120 slides towards the distal end of first chamber 164. The applied force ($F_1$) produces a positive pressure (P) on the hydraulic fluid (S) with respect to the ambient pressure. The pressure (P) produced on hydraulic fluid (S) within first chamber 164 is calculated based on Equation (1):

$$P = F_1/A_1 \qquad (1)$$

where $A_1$ is the transverse cross sectional area of manual plunger 120 which is exposed to the hydraulic fluid. In the present embodiment, area ($A_1$) is thus also equal to the transverse cross sectional area of first chamber 164.

This resulting pressure (P) of the hydraulic fluid is exerted against head 181 of hydraulic plunger 180 which causes hydraulic plunger 180 to slide distally within second chamber 165. Head 181 has a transverse cross sectional area ($A_2$) which is exposed to the hydraulic fluid. In the present embodiment, area ($A_2$) is equal to the transverse cross sectional area of second chamber 165. As hydraulic plunger 180 slides distally, hydraulic fluid (S) fills within second chamber 165. As a result of area ($A_2$) being larger than area ($A_1$), a resulting increased force ($F_2$) is applied on hydraulic plunger 180 through a hydraulic advantage. This force ($F_2$) is not only the force that is applied to hydraulic plunger 180 but is also the force, as discussed below, that hydraulic plunger 180 uses to dispense viscous fluids from syringe 100. The hydraulic force ($F_2$) is calculated based on the following Equation (2):

$$F_2 = F_1 \times A_2/A_1 \qquad (2)$$

Thus, if the transverse cross sectional area ($A_2$) of hydraulic plunger 180 is twice as big as the transverse cross sectional area ($A_1$) of manual plunger 120, force $F_2$ is twice as big as the force $F_1$ applied to handle 110. As a result of this hydraulic advantage producing a larger force on hydraulic plunger 180, it is easier for a user of syringe 100 to dispense highly viscous fluids at a constant and steady rate using minimal force and exertion.

In one embodiment, the diameter $D_1$ of first chamber 164 is in a range between about 0.8 inches (2 cm) to about 0.02 inches (0.05 cm), with about 0.4 inches (1 cm) to about 0.1 inches (0.25 cm) being more preferred. The diameter $D_2$ of second chamber 165 is typically in a range between about 2 inches (5 cm) to about 0.07 inches (0.2 cm), with about 0.8 inches (2 cm) to about 0.2 inches (0.5 cm) being more preferred. The ratio of $A_2/A_1$ is typically in a range between about 1 to about 7, with about 3 to about 5 being more preferred. The above dimension, of course, are only by way of example and can change dramatically depending on the intended use.

The present invention envisions that there are a variety of alternative embodiments that can be used to achieve the hydraulic advantage. For example, although the transverse cross-sectional shape of the first and second chambers is shown as being circular, chambers of any configuration in which a plunger can slide are equivalent. It is evident, of course, that the corresponding plungers will need to have complementary shapes. Other embodiments for achieving a hydraulic advantage are disclosed below.

It is also noted that the difference in the transverse cross sectional area between the first chamber and the second chamber can be very slight or large and in both embodiments a hydraulic advantage is obtained. The smaller the variance, the smaller the hydraulic advantage. The actual size of the syringe and the variance between the transverse cross sectional areas of the plungers is dependent in part on the type, viscosity, and amount of fluid to be dispensed.

The depicted embodiment discloses the manual and hydraulic plungers sliding along a common longitudinal axis (X). The present invention also envisions that the plungers can slide along non-common axises. Furthermore, the sliding direction of the hydraulic plunger may be other than the direction of the manual plunger.

The present invention also envisions that there are a variety of alternative embodiments for coupling the viscous material with syringe 100 for dispensing by hydraulic plunger 180. For example, depicted in FIGS. 2 and 3, an end cap 200 includes a base plate 203 having an aperture 201 extending there through. Aperture 201 is configured to receive shaft 182 of hydraulic plunger 180. Projecting from the front face of base plate 203 is an annular collar 204 having a pair of bayonet slots 202 formed therein. End cap 200 is fitted within an annular grooved slot 206 formed within second chamber 165. A flexible C-shaped locking clip 210 is also disposed within grooved slot 206 to prevent inadvertent removal of end cap 200 from syringe barrel 160. An annular seal 190 is biased between end cap 200 and syringe barrel 160 to effect a secure, snug fitting. In this configuration, shaft 182 of hydraulic plunger 180 is disposed within and/or aligned with aperture 201 of end cap 200.

Nozzle 230, which in one embodiment comprises a disposable cartridge, includes a sidewall 223 extending from a proximate end 224 to and opposing distal end 225. Sidewall 223 bounds an interior compartment in which the material for dispensing is disposed. Outwardly projecting from proximal end 224 are a pair of bayonet connectors configured for selective locking with bayonet slots 202. Formed at distal end 225 is an outlet orifice through which the material is expelled. In the embodiment depicted, a nozzle plunger 220 is slidably disposed within proximal end 224 of nozzle 230.

Prior to attachment of nozzle 230, manual plunger 120 is pulled back into its most proximate position such that hydraulic plunger 180 is also pulled back into its proximate position. In this position, nozzle 230 is mechanically locked into end cap 200 by inserting bayonet connectors 232 into bayonet slots 202 of end cap 200 and slightly twisting nozzle 230 about the longitudinal axis (X).

To facilitate dispensing, manual plunger 120 is advanced which in turn advances hydraulic plunger 180 under a hydraulic force as previously discussed. As hydraulic plunger 180 advances, shaft 182 pushes against nozzle plunger 220 which in turn advances nozzle plunger 220 within nozzle 230. As nozzle plunger 220 advances, the dispensing material disposed therein is ejected out through orifice 231. In alternative embodiments, nozzle plunger 220 can be removed and shaft 182 can function as the plunger for directly dispensing the material from nozzle 230.

In yet another embodiment, it is also envisioned that a nozzle tip can be threadedly or otherwise removably mounted directly to distal end 153 of syringe barrel 160. The dispensing material can then be selectively positioned within second chamber 165 when hydraulic plunger 180 is in the proximate position. By advancing plungers 120 and 180, cylindrical head 181 of hydraulic plunger 180 functions to press the material out of the nozzle tip. In this embodiment, it is envisioned that shaft 182 can be removed from head 181. In alternative embodiments, shaft 182 can have the same diameter as head 181.

The present invention includes means for hydraulically producing an increased force against dispensing material within nozzle 230 when an initial force is applied to manual plunger 120, the increased force being greater than the initial force. One example of such means includes hydraulic plunger 180 having the transverse cross sectional area $A_2$ greater than the transverse cross sectional area $A_1$ of manual plunger 120, as previously discussed with regard to FIGS. 3 and 4.

Figure 5:
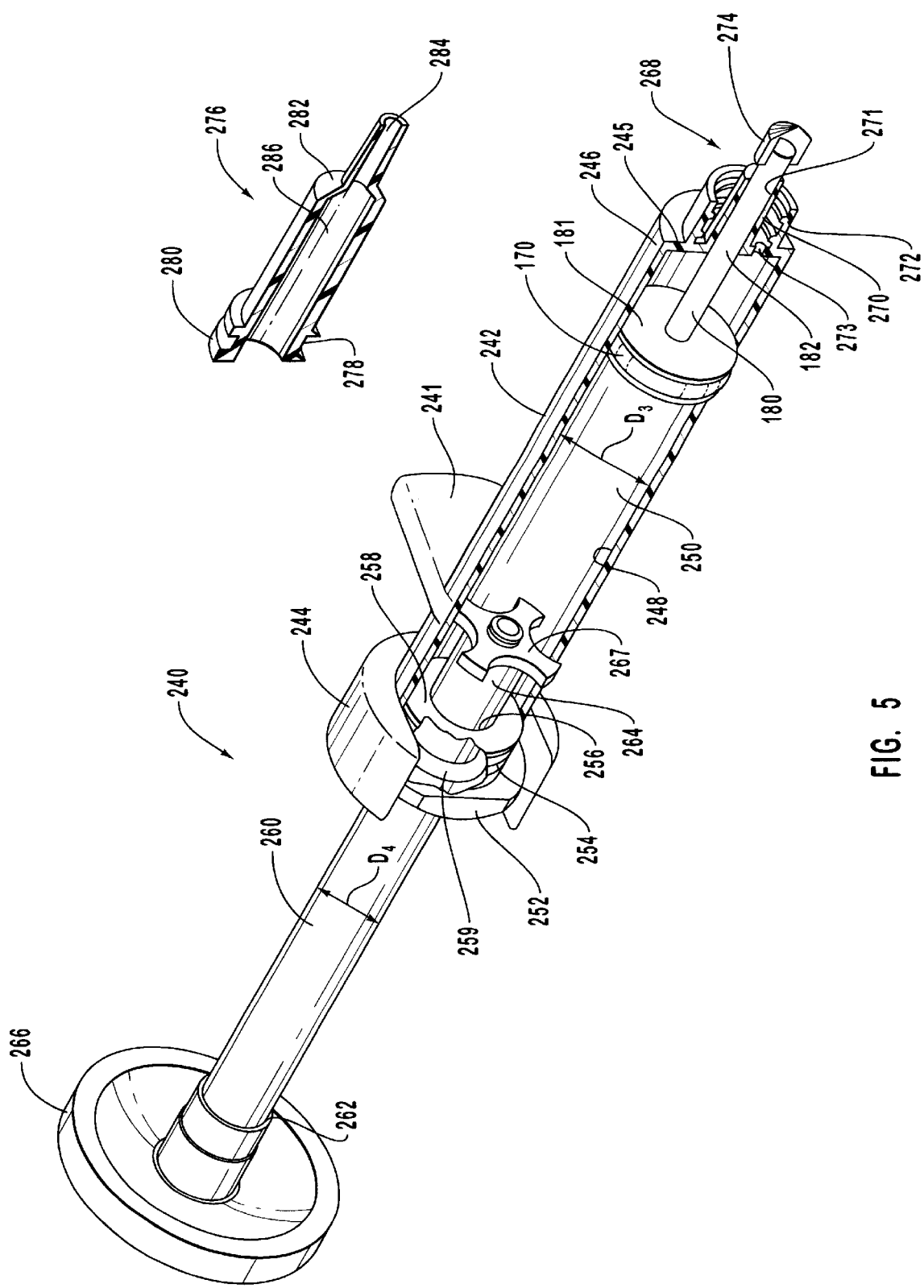
FIG. 5 is a partial cross section isometric view of an alternative embodiment of a hydraulic syringe, wherein the barrel has a single chamber.

The present invention, however, envisions that there are a variety of alternative plunger and barrel configuration that also function to hydraulically produce an increased force against the dispensing material. For example, depicted in FIG. 5 is an alternative embodiment of an inventive syringe 240 that is also configured to produce a hydraulic advantage for dispensing highly viscous material. Syringe 240 includes a barrel 242 longitudinally extending from a first end 244 to an opposing second end 246. Barrel 242 has an interior surface 248 that bounds a chamber 250. In the embodiment depicted, chamber 250 has a substantially cylindrical configuration having a diameter $D_3$ and a corresponding transverse cross sectional area.

Outwardly projecting from the side of barrel 242 are finger grips 241. Barrel 242 terminates at second end 246 at an end wall 245. Outwardly projecting from end wall 245 is a female coupler 268. Coupler 268 includes a tubular spout 270 encircled by a threaded sleeve 272. In one embodiment, coupler 268 comprises a portion of a Luer Lock connector. Spout 270 bounds a passageway 271 that facilitates communication between chamber 250 and the exterior. A vent port 273 extends through end wall 245 and exits between spout 270 and threaded sleeve 272. In alternative embodiments, vent port 273 can exit outside of sleeve 272.

Threadedly mounted at first end 244 of barrel 242 is a tubular bushing 252. Bushing 252 has an exterior surface 254 that is sealed against interior surface 248 of barrel 242. Bushing 252 also has an interior surface 256 that bounds an opening 258 extending there through. A seal 259 is mounted on interior surface 256 so as to encircle opening 258.

Slidably disposed within opening 258 of bushing 252 is a manual plunger 260 having an elongated, substantially cylindrical shaft-like configuration. Manual plunger 260 has a first end 262, an opposing second end 264, and a diameter $D_4$ with a corresponding transverse cross sectional area. Diameter $D_4$ and corresponding transverse cross sectional area of manual plunger 260 are smaller than diameter $D_3$ and corresponding transverse cross sectional area of chamber 250.

Mounted at first end 262 of manual plunger 260 is an enlarged handle 266. Second end 264 of manual plunger 260 is disposed within chamber 250 of barrel 242. Radially outwardly projecting from second end 264 of manual plunger 260 is a guide 267. Guide 267 facilitates alignment of manual plunger within chamber 250 and prevents accidental removal of manual plunger 260 through bushing 252. Manual plunger 260 is biased in sealed engagement against o-ring 259. As such, a liquid tight seal is maintained between manual plunger 260 and bushing 252 as manual plunger 260 is selectively advanced and retracted through bushing 252.

Slidably disposed within second end 246 of chamber 250 is hydraulic plunger 180. Hydraulic plunger 180 and its corresponding elements were previously discussed with regard to FIGS. 2 and 3. As depicted in FIG. 5, o-ring 170 mounted on head 181 of hydraulic plunger 180 is slidably biased in sealed engagement against interior surface 248 of chamber 250. As such, hydraulic plunger 180 has a maximum diameter and corresponding transverse cross sectional area substantially equal to diameter $D_3$ and the corresponding transverse cross sectional area of chamber 250. Mounted at the end of shaft 182 projecting from head 181 is a sealing bulb 274.

Removably coupled with second end 246 of barrel 242 is a nozzle 276. Nozzle 276 has a first end 278 with threads 280 outwardly projecting therefrom. Nozzle 276 also has an opposing second end 282 with a constricted exit orifice 284 formed thereat. Nozzle 276 bounds a compartment 286 configured to hold a dispensing material. Nozzle 276 is configured such that first end 278 of nozzle 276 can be threadedly engaged with threaded sleeve 272. In this configuration, spout 270 and sealing bulb 274 are received within compartment 286 of nozzle 276. Sealing bulb 274 is configured to bias in sealed engagement against the interior surface bounding compartment 286 as bulb 274 is advanced and retracted within compartment 286.

During operation, a hydraulic fluid is sealed between bushing 252 and head 181 of hydraulic plunger 180. As manual plunger 260 is advanced within chamber 250 of barrel 242, the pressure on the hydraulic fluid is increased. In turn, the hydraulic fluid presses against hydraulic plunger 180, thereby slidably advancing hydraulic plunger 180 towards end wall 245 of barrel 242. As hydraulic plunger 180 advances, the air between head 181 and end wall 245 escapes through vent port 273. Furthermore, as hydraulic plunger 180 advances, bulb 274 advances within chamber 286 of nozzle 276, thereby pressing the material contained therein out through exit orifice 284.

Because manual plunger 260 has a substantially uniform transverse cross sectional area that is smaller than the transverse cross sectional area of head 181, advancing manual plunger 260 under a first force at a first speed result in a hydraulic change or advantage which moves hydraulic plunger 180 under a second force, which is greater than the first force, and at a second speed, which is slower than the first speed. As a result, syringe 240 is effective for dispensing highly viscous material in a controlled manner using minimal exertion.

Depicted in FIG. 6 is yet another embodiment of an inventive syringe 290 which produces a desired hydraulic advantage. Syringe 290 includes a barrel 292. Barrel 292 includes an outer barrel 294 and an inner barrel 296. Outer barrel 294 has an interior surface 298 that bounds a chamber 304 and extends between an first end 300 and an opposing second end 302. Outwardly projecting from first end 300 of outer barrel 294 is an annular flange 306. Flange 306 has an annular front face 305 that terminates at an annular ridge 307. Front face 305 is substantially flat and is disposed in a plane perpendicular to the longitudinal axis of syringe 290. Flange 306 also includes an annular back face 309 that inwardly slopes from ridge 307 to the outer surface of outer barrel of 294.

Outer barrel 294 terminates at second end 302 at an end wall 315. Extending through end wall 315 is a vent port 317. Projecting from end wall 315 is female coupler 268, as previously discussed with regard to FIG. 5. Finger grips 308 outwardly project from outer barrel 294 between first end 300 and opposing second end 302.

Inner barrel 296 includes an elongated tubular sleeve 310 having an interior surface 312 and an exterior surface 314 each extending between a first end 316 and an opposing second end 318. Exterior surface 314 of tubular sleeve 310 has a configuration substantially complementary to interior surface 298 of outer barrel 294. As such, tubular sleeve 310 is selectively slid within outer barrel 294. Encircling tubular sleeve 310 is an annular seal 311. Seal 311 produces a liquid tight seal between exterior surface 314 of tubular sleeve 310 and interior surface 298 of outer barrel 294.

Inner barrel 296 also includes a substantially U-shaped clamp 320 encircling and outwardly projecting from first end 316 of tubular sleeve 310. As depicted in FIG. 7, clamp 320 includes an annular first arm 322 radially outwardly projecting from first end 316 of tubular sleeve 310; an annular second arm 324 projecting from the distal end of first arm 322 in substantially parallel alignment with the longitudinal axis of syringe 290; and an annular third arm 326 inwardly projecting from the distal end of second arm 324. Third arm 326 terminates an annular ridge 328 and includes an annular engagement face 330 that outwardly slopes from annular ridge 328.

During assembly, second end 318 of inner barrel 296 is slidably received within outer barrel 294. Inner barrel 296 is advanced until engagement face 330 of clamp 320 contacts annular ridge 307 of flange 306. As a result of engagement face 330 being sloped, additional force on inner barrel 296 results in radial outward expansion of third arm 326 until annular ridge 328 of clamp 320 passes over annular ridge 307 of flange 306. Third arm 326 then resiliently inwardly constricts to bias against back face 309 of flange 306, thereby mechanically securing outer barrel 294 and inner barrel 296 together. As a result of back face 309 being inwardly sloped, third arm 326 is urged forward to maintain a secure engagement. In one embodiment, the engagement between outer barrel 294 and inner barrel 296 is sufficient to produce a liquid tight seal therebetween. In alternative embodiments, seal 311 can be used.

As depicted in FIGS. 6 and 7, interior surface 312 of inner barrel 296 bounds a first chamber 332 longitudinally extending through inner barrel 296. First chamber 332 has a substantially cylindrical configuration with an inner diameter $D_5$. An annular groove 334 is formed on interior surface 312 of inner barrel 296 at first end 316. Disposed adjacent to annular groove 334 is an inwardly projecting annular shoulder 346. Disposed within groove 334 is an annular seal 336.

Slidably disposed within first chamber 332 is a manual plunger 338. Manual plunger 338 has a first end 340 with a handle 342 disposed thereat and an opposing second end 344 disposed within first chamber 332. Manual plunger 338 has a substantially cylindrical shaft-like configuration having a diameter $D_6$. Manual plunger 338 is slidably biased against seal 336 so as to affect a liquid tight seal between manual plunger 338 and inner barrel 296 at seal 336. Disposed at second end 344 of manual plunger 338 is a guide 348. Guide 348 has a diameter slightly larger than the diameter of manual plunger 338 and is configured to hit against shoulder 346 so as to prevent manual plunger 338 from accidentally being pulled out of barrel 290. Guide 348 also facilitates alignment of manual plunger within barrel 292. In alternative embodiments, guide 348 may or may not effect a liquid tight seal against interior surface 312 of inner barrel 296.

As depicted in FIGS. 6 and 7, inner barrel 296 has a shorter length than outer barrel 294. As a result, a substantially cylindrical second chamber 350 is formed between inner barrel 296 and an end wall 315 of outer barrel 294. Second chamber 350 has a diameter $D_7$ that is larger than diameter $D_6$ of manual plunger 338. Slidably disposed within second chamber 350 is hydraulic plunger 180 as previously discussed with regard to FIG. 5. Seal 170 mounted on head 181 of hydraulic plunger 180 is slidably biased in sealed engagement against interior surface 298 of outer barrel 294 bounding second chamber 350. As such, hydraulic plunger 180 as used in FIGS. 6 and 7 has a maximum diameter substantially equal to diameter $D_7$ of second chamber 350.

Nozzle 276 as previously discussed with regard to FIG. 5 is secured to second end 302 of outer barrel 294. Shaft 182 and bulb 274 are disposed within compartment 286 such that as hydraulic plunger 180 is advanced, bulb 274 pushes material within compartment 286 out orifice 284.

During operation, as previously discussed with the other inventive syringes, a hydraulic fluid is sealed between seal 336 and head 181 of hydraulic plunger 180. As manual plunger 338 is advanced within first chamber 332, the pressure on the hydraulic fluid is increased. In turn, the hydraulic fluid presses against hydraulic plunger 180, thereby slidably advancing hydraulic plunger 180 towards end wall 315 of outer barrel 294. In an alternative embodiment, plunger 338 can also be configured to advance into second chamber 350.

Because manual plunger 338 has a substantially uniform transverse cross sectional area that is smaller than the transverse cross sectional area of head 181, advancing manual plunger 338 under a first force at a first speed result in a hydraulic change or advantage which moves hydraulic plunger 180 under a second force, which is greater than the first force, and at a second speed, which is slower than the first speed. As a result, syringe 290 is effective for dispensing highly viscous material in a control manner using minimal exertion.

Figure 8:
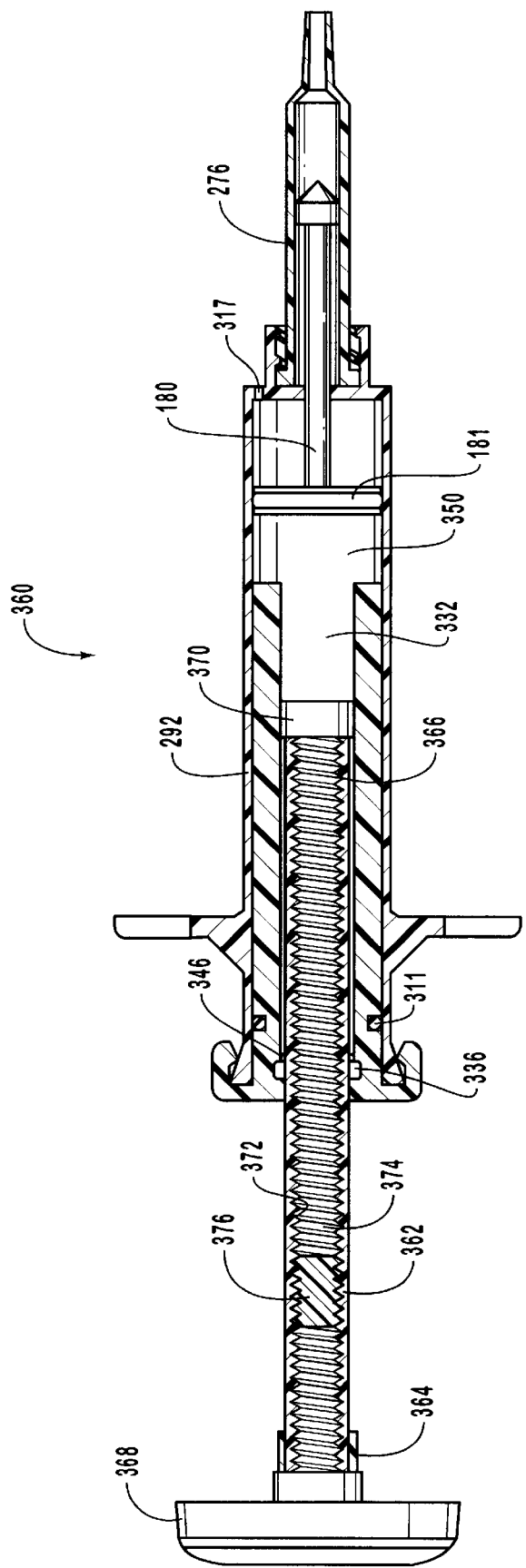

Depicted in FIG. 8 is yet another embodiment of an inventive syringe 360. Syringe 360 includes barrel 292, nozzle 276, and hydraulic plunger 180 as previously discussed with regard to syringe 290 in FIGS. 6 and 7. In contrast to syringe 290, however, syringe 360 has a uniquely configured manual plunger 362. Manual plunger 362 has a substantially cylindrical shaft-like configuration that extends from a first end 364 to an opposing second end 366. Removably attached to first end 364 of plunger 362 is a handle 368. Handle 368 can be removably attached in any conventional manner such as by threaded, chemical, or frictional engagement. Radially outwardly projecting from second end 366 of manual plunger 362 is a guide 370. Guide 370 is configured to hit against shoulder 346 so as to prevent accidental removal of manual plunger 362 from barrel 292. Guide 370 can be integrally formed with or separately attached to manual plunger 362.

Manual plunger 362 also includes an threaded interior surface 372 bounding a channel 374 longitudinally extending through manual plunger 362. Threadedly disposed within channel 374 is a plug 376. Plug 376 is configured to produce a liquid tight seal with manual plunger 362 so as to occlude channel 374.

During operation, a hydraulic fluid is disposed within barrel 292 between seal 336 and head 181 of hydraulic plunger 180 so as to fill channel 374 up to plug 376. As manual plunger 362 is advanced within chambers 332 and 350, hydraulic plunger 180 is advanced under a hydraulic advantage as previously discussed with regard to FIGS. 6 and 7. On occasion, however, a portion of the hydraulic fluid may leak around seal 336, head 181, and/or plug 376. To compensate for the loss of hydraulic fluid, handle 368 is removed and a tool, such as a screwdriver, is used to advance plug 376 within channel 374, thereby eliminating the space that was previously occupied by the lost hydraulic fluid. Alternatively, plug 376 can be removed and additional hydraulic fluid can be added.

Figure 9:
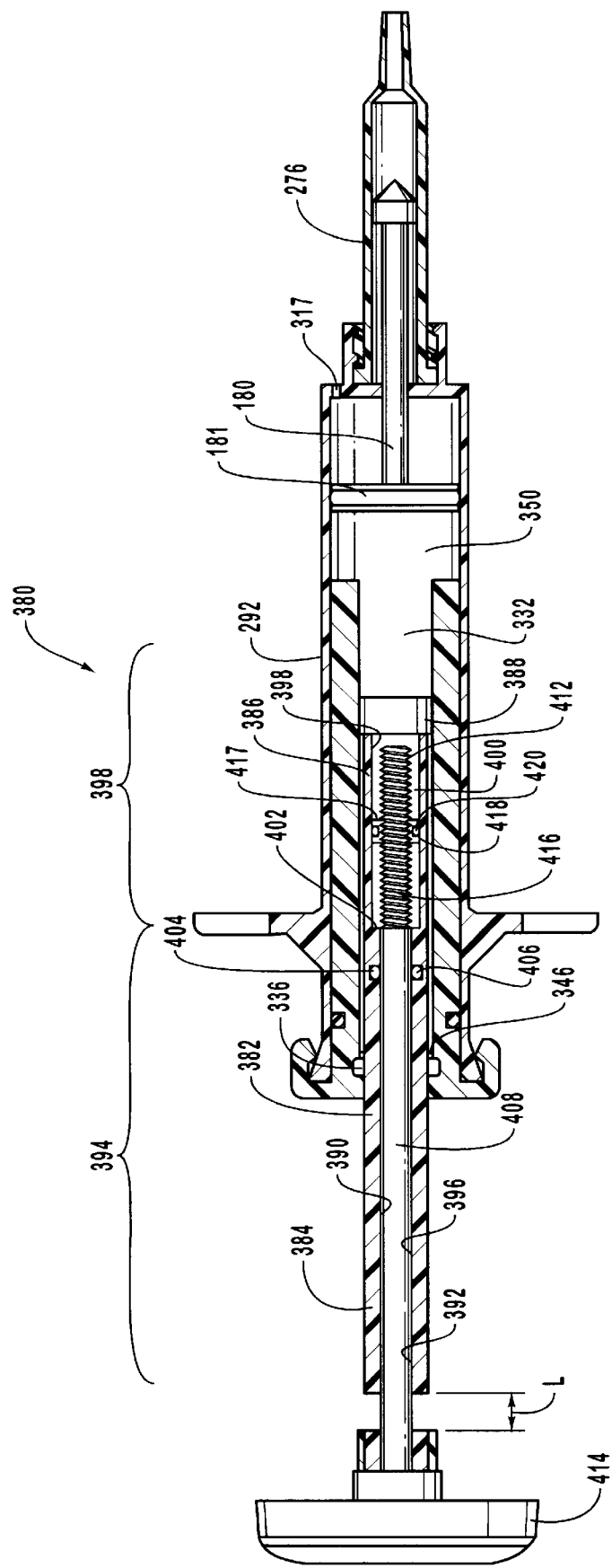
FIG. 9 is a cross sectional side view of an alternative embodiment of a hydraulic syringe having a slidable rod disposed within the manual plunger.

Depicted in FIG. 9 is yet another embodiment of an inventive syringe 380 incorporating features of the present invention. Syringe 380 is substantially identical to syringe 290 discussed with regard to FIGS. 6 and 7. As such, like elements will be referenced with like reference characters. Syringe 380 is distinguished from syringe 290 in that syringe 380 has a unique manual plunger 382. Manual plunger 382 has a substantially cylindrical shaft-like configuration that extends from a first end 384 to an opposing second end 386. Radially outwardly projecting from second end 386 of manual plunger 382 is a guide 388. Guide 388 is configured to hit against shoulder 346 so as to prevent accidental removal of manual plunger 382 from barrel 292. Guide 388 can be integrally formed with or separately attached to manual plunger 382.

Manual plunger 382 also includes an interior surface 390 bounding a channel 392 longitudinally extending through manual plunger 382. Interior surface 390 includes a cylindrical first portion 394 disposed at first end 384 that bounds a first channel 396 and a cylindrical second portion 398 disposed at second end 388 that bounds a second channel 400. Second channel 400 has a diameter greater than the diameter of first channel 396 such that a shoulder 402 is formed therebetween. An annular groove 404 is formed on first portion 394 of interior surface 390. Disposed within annular groove 404 is a seal 406.

Disposed within channel 392 is a rod 408. Rod 408 is biased against seal 406 so as to effect a liquid tight seal between rod 408 and manual plunger 382 at seal 406. Rod 408 has a first end 410 and an opposing second end 412. First end 410 of rod 408 projects past first end 384 of manual plunger 382 and has a handle 414 attached thereto. A pretravel distance L extends between handle 414 and first end 384 of manual plunger 382.

Second end 412 of rod 408 is disposed within second channel 400 and has threads 416 formed thereon. Also disposed within second channel 400 is an adjusting collar 417. Adjusting collar 417 encircles and is threadedly engaged to second end 412 of rod 408 so as to effect a liquid tight seal therewith. Adjusting collar 417 also has an annular exterior surface 418 on which a seal 420 is disposed. Seal 420 is slidable disposed against second portion 398 of interior surface 390 so as to effect a liquid tight seal between adjusting collar 417 and interior surface 390. As such, adjusting collar 417 and seal 420 produce a liquid tight seal between rod 408 and interior surface 390 of second portion 398.

During operation, a hydraulic fluid is disposed within barrel 292 between seal 336 and head 181 of hydraulic plunger 180 so as to fill second channel 400 up to seal 420. Initially, as handle 414 is advanced, only rod 408 is advanced within channel 392 of manual plunger 382. As rod 408 advances within channel 392, the hydraulic fluid is pressurized. In turn, the pressurized hydraulic fluid begins the advancement of hydraulic plunger 180 and thus the dispensing of material from within nozzle 276. Once handle 414 completes its movement over the pretravel distance L, handle 414 hits against manual plunger 382. As such, manual plunger 382 and rod 408 are advanced within chambers 332 and 350, so as to further advance hydraulic plunger 180.

Since both rod 408 and manual plunger 382 have a diameter that is smaller than the diameter of head 181 of hydraulic plunger 180, the advancement of rod 408 and the combination of rod 408 and manual plunger 382 produce a hydraulic advantage in moving hydraulic plunger 180. That is, application of a first force to handle 414 results in the application of a second greater force to hydraulic plunger 180. One of the benefits of advancing rod 408 independent of manual plunger 382 is that since rod 408 has a small diameter and thus smaller transverse cross sectional area than the combination of rod 408 and manual plunger 382, a greater hydraulic advantage is obtained by initially using rod 408. This greater hydraulic advantage is useful in overcoming the static friction in getting the dispensing material and hydraulic plunger 180 moving. Once these items begin moving, less force is required to maintain their movement. As such, manual plunger 382 can then be added which decreases the hydraulic advantage but increases the rate at which the dispensing material is dispensed.

By rotating rod 408, adjusting collar 417 can be selectively positioned along the length of second end 412 of rod 408. This movement of adjusting collar 417 can be used to compensate for the loss of any hydraulic fluid from barrel 292.

Depicted in FIG. 10 is yet another embodiment of an inventive syringe 430 incorporating features of the present invention. Syringe 430 includes a barrel 432 extending from a first end 434 to an opposing second end 436. Integrally molded with and radially projecting out from barrel 432 are a pair of finger grips 438. Barrel 432 has an interior surface 440 bounding a chamber 442. Chamber 442 communicates with the exterior through an inlet port 444 positioned at first end 434 and an opposing outlet port 446. Outlet port 446 extends through an end wall 447 positioned at second end 436.

Syringe 430 also includes a manual plunger 448. Manual plunger 448 has a substantially cylindrical shaft-like configuration and extends from a first end 452 to an opposing second end 454. Secured at first end 452 of manual plunger 448 is a handle 456. Second end 454 of manual plunger 448 is slidably disposed within chamber 442. A guide 458 is secured to second end 454 of manual plunger 448 and is also slidably disposed within chamber 442. As depicted in FIG. 11, guide 458 encircles manual plunger 448 and includes a plurality of radially outwardly projecting fins 460. Each fin 460 extends either adjacent to or in direct contact with interior surface 440 of barrel 432. Extending between each fin 460 is a channel that allows fluid to pass between each of fins 460 as manual plunger 448 is slidably moved back and forth within chamber 442.

Figure 12:
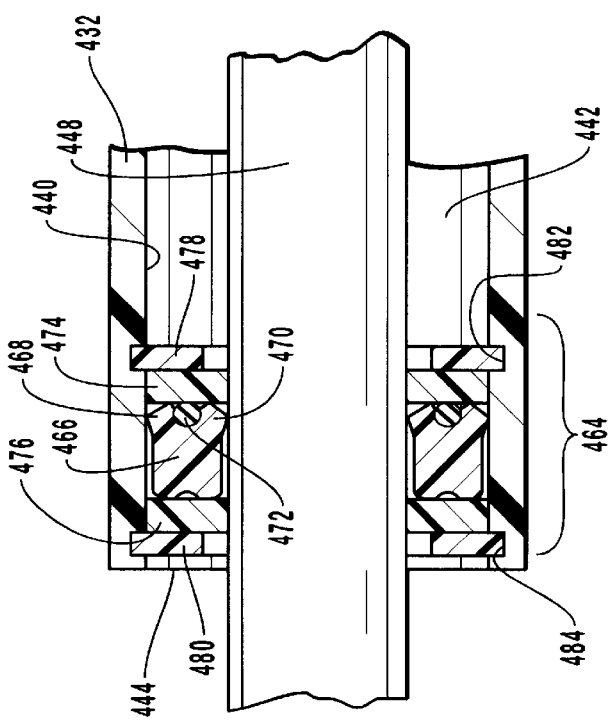
FIG. 12 is a cross sectional side view of the sealing assembly shown in FIG. 10.

In one embodiment, guide 458 is made of brass and is pressure-fit onto manual plunger 448. In alternative embodiments, guide 458 can be formed from a variety of non-corrosive materials such as stainless steel or different plastics and can be secured in any conventional manner known to those skilled in the art. Guide 458 functions in part to minimize lateral displacement of second end 454 of manual plunger 448. Furthermore, as discussed below in greater detail, guide 458 functions to prevent second end 454 of manual plunger 448 from accidentally being withdrawn from inlet port 444 of barrel 432. Encircling manual plunger 448 at first end 434 of barrel 432 is a sealing assembly 464. Depicted in FIG. 12, sealing assembly 464 includes an annular seal 466 encircling manual plunger 448. In the embodiment depicted, seal 466 comprises a loaded lip seal with bevel lip, such as a Pip Seal. Seal 466 has an outside wing 468 and an inside wing 470 each facing second end 436 of barrel 432. Outside wing 468 is biased in sealed engagement against interior surface 440 of barrel 432. Inside wing 470 is biased in sealed engagement against manual plunger 448. An elastic o-ring 472 is disposed between inside wing 470 and outside wing 468. In alternative embodiments, seal 466 can comprise any other conventional seal or sealing material as previously discussed.

Seal 466 is retained between an annular inside washer 474 and an annular outside washer 476. Each washer 474 and 476 encircles manual plunger 448 so as to enable manual plunger 448 to slidably move therethrough. In turn, washers 474 and 476 are retained between an inside C-clip 478 and an outside C-clip 480. Inside C-clip 478 is secured within an annular groove 482 recessed on interior surface 440 of barrel 432. Similarly, outside C-clip 480 is secured within an annular groove 484 recessed within interior surface 440 of barrel 432.

During assembly, inside C-clip 478 is disposed within groove 482 following which inside washer 474, seal 466, and outside washer 476 are slidably disposed within chamber 442. Finally, outside C-clip 480 is fit into groove 484. The positioning of C-clips 478 and 480 maintains seal 466 continually retained between washers 474 and 476. In one embodiment, interior surface 440 of barrel 432 radially outwardly slopes from the position of seal 466 to inlet port 444. The outward slope typically has an inside angle in a range between about 1° to about 100 and preferably in a range between about 2° to about 5°. This outward sloping of interior surface 440 makes it easier to insert seal 466 within chamber 442 without damaging seal 466.

Sealing assembly 464 not only functions to produce a liquid tight seal between manual plunger 448 and barrel 432, but it also interacts with guide 458 to prevent accidental removal of manual plunger 448. That is, as manual plunger 448 is drawn back, guide 458 hits against inside C-clip 478 and/or inside washer 474 to prevent further withdrawal of manual plunger 448.

Figure 13:
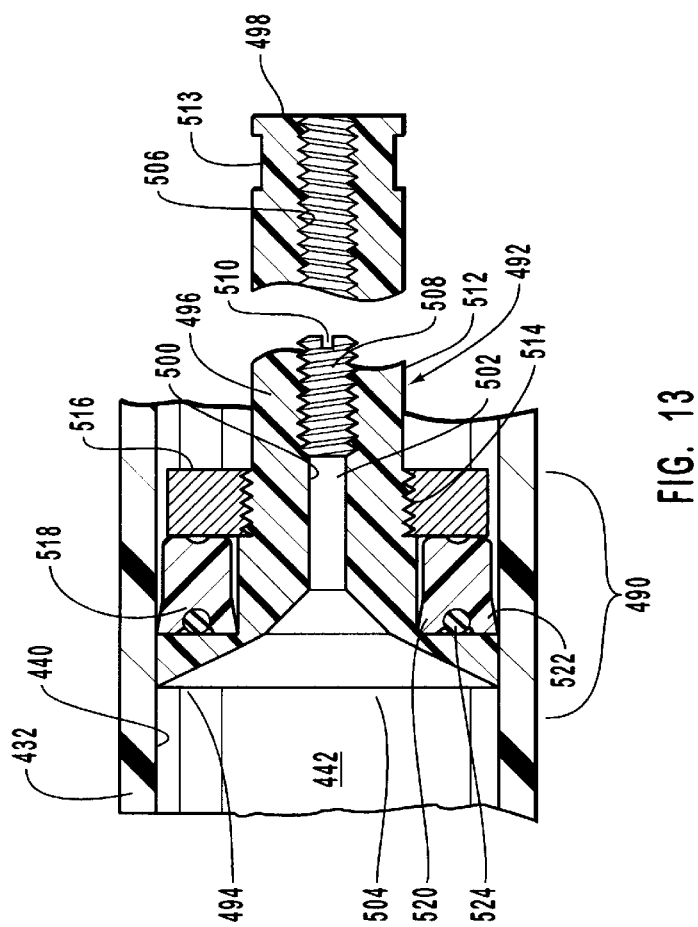
FIG. 13 is a cross sectional side view of the hydraulic plunger shown in FIG. 10.

Returning back to FIG. 10, syringe 430 also includes a hydraulic plunger 490 slidably disposed within second end 436 of chamber 442. As depicted in FIG. 13, hydraulic plunger 490 includes a piston 492 having an enlarged annular head 494. A tubular shaft 496 extends from head 494 to a freely exposed terminus 498. Shaft 496 is slidably disposed within outlet port 446 so as to extend through end wall 447 (FIG. 10). Shaft 496 has an interior surface 500 bounding a channel 502 longitudinally extending therethrough. Channel 502 is in fluid communication with a substantially conical, radially inwardly sloping opening 504 extending through head 494. Formed on interior surface 500 of shaft 496 is a threaded portion 506. Threadedly disposed within threaded portion 506 is a plug 508. Plug 508 seals against threaded portion 506 so as to occlude channel 502. Plug 508 has a slot 510 formed in the end thereof which enables plug 508 to be selectively advanced along or removed from channel 502 by used of a screw driver or other corresponding tool inserted into channel 502 from terminus 498.

Piston 492 also has an exterior surface 512 having a threaded portion 514 formed thereon. A pair of opposing flats 513 are also formed on exterior surface 512 toward terminus 498. Flats 513 enable the use of a wrench or other tool to hold piston 492 stationary as plug 508 is rotated into or out of channel 502. An annular restraining nut 516 encircles piston 492 and is threadedly engaged with threaded portion 514. Disposed between retraining nut 516 and head 494 of piston 492 is a seal 518. Seal 518 is comparable to seal 466 and can comprise a loaded lip seal, an o-ring, or any other conventional sealing structure as previously discussed. In the embodiment depicted, seal 518 has an inside wing 520 and an outside wing 522 each facing towards first end 535 of barrel 432. Disposed between wings 520 and 522 is an elastic o-ring 524. Restraining nut 516 is screwed onto piston 492 so as to retain seal 518 between restraining nut 518 and head 494. As a result, inside wing 520 is biased in sealed engagement against piston 492 and outside wing 522 is biased and sealed engagement against interior surface 440 of barrel 432.

Returning back to FIG. 10, chamber 442 is divided into a first compartment 526 and a second compartment 528. First compartment 526 extends from sealing assembly 464 to hydraulic plunger 490. Second compartment 428 extends from seal 518 to end wall 447. The relative sizes of first compartment 526 and second compartment 528 depends on the position of hydraulic plunger 490 along the length of barrel 432. Disposed within first compartment 426 is a hydraulic fluid 530 such as that previously discussed. Accordingly, for substantially the same reasons as previously discussed with regard to the hydraulic syringes 240, 290, 360, and 380, as manual plunger 448 is advanced within first compartment 526 under a first manual force, hydraulic plunger 490 is advanced under an increased second force as a result of the hydraulic pressure produced by hydraulic fluid 530 within first compartment 526.

Should a portion of hydraulic fluid 530 leak from first compartment 526, plug 508 (FIG. 13) can be manually removed, as previously discussed, and additional hydraulic fluid 530 added through channel 502. Conical opening 504 helps to remove any air bubbles within first compartment 526 prior to replacement of plug 508.

Figure 15:
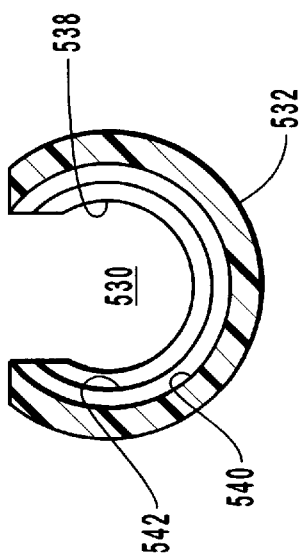
FIG. 15 is a cross sectional side view of the mounting arm projecting from the end of the syringe shown in FIG. 10.
Figure 14:
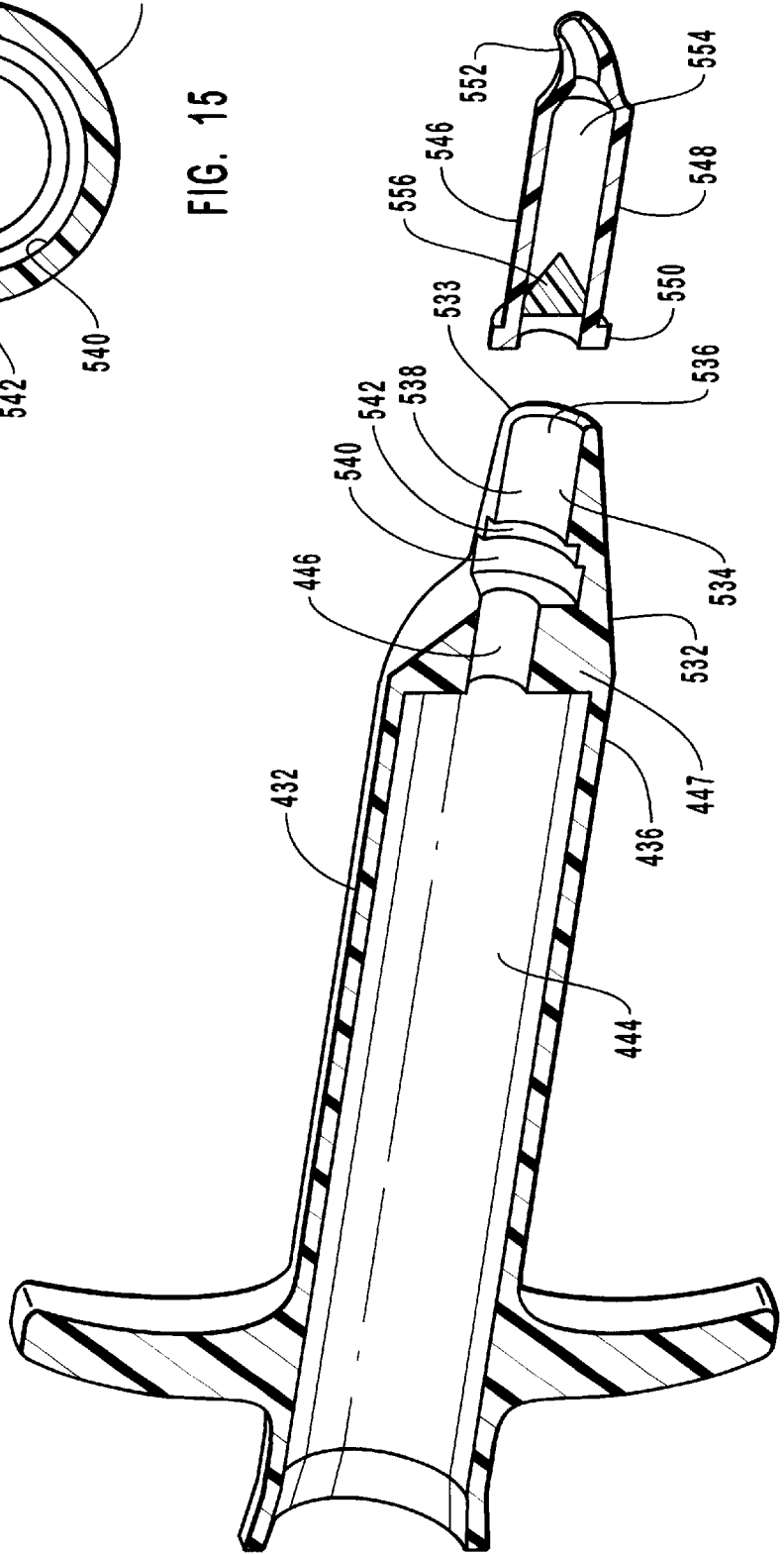
FIG. 14 is cross sectional side view of the cartridge shown in FIG. 10 separated from the syringe barrel.

As depicted in FIGS. 10, 14, and 15, an elongated mounting arm 532, having a substantially U-shaped transverse cross section, projects from end wall 447 to a free tip 533. Mounting arm 532 has an interior surface 534 that bounds a substantially U-shaped channel 536. Channel 536 is aligned with outlet port 446. Interior surface 534 includes a retention seat 538 disposed adjacent to tip 533, a radially enlarged groove 540 disposed adjacent to end wall 447, and a transition shoulder 542 disposed between retention seat 538 and enlarged groove 540.

Channel 536 is configured to receive a nozzle in the form of cartridge 546. Cartridge 546 includes a barrel 548 having a annular flange 550 radially outwardly projecting from one end and a curved spout 552 projecting from the opposing end. Barrel 548 bounds a chamber 554 configured to receive a viscous or other material for dispensing. Slidably disposed within chamber 554 is a plunger 556.

During dispensing, cartridge 546 is positioned within channel 536 such that flange 550 is received within groove 540 and barrel 548 is received within retention seat 538. As depicted in FIG. 15, retention seat 538 is undercut and has a configuration that is complementary to the exterior of barrel 548. As a result, retention seat 538 of mounting arm 532 snap-fits around barrel 548 of cartridge 546 so as to removably secure cartridge 546 when cartridge 546 is received within channel 530. In this configuration, as hydraulic plunger 490 is advanced, shaft 496 is advanced within cartridge 546 so as to advance plunger 556 therein. In turn, plunger 556 pushes the dispensing material out through spout 552.

Alternative embodiments of and further disclosure with regard to mounting arm 532 and cartridge 546 are disclosed in U.S. Pat. Nos. 4,295,828; 4,330,280; 4,384,853; 4,4,767, 326; 391,590; and 5,707,234 which for purposes of disclosure are hereby specifically incorporated by reference.

Figure 16:
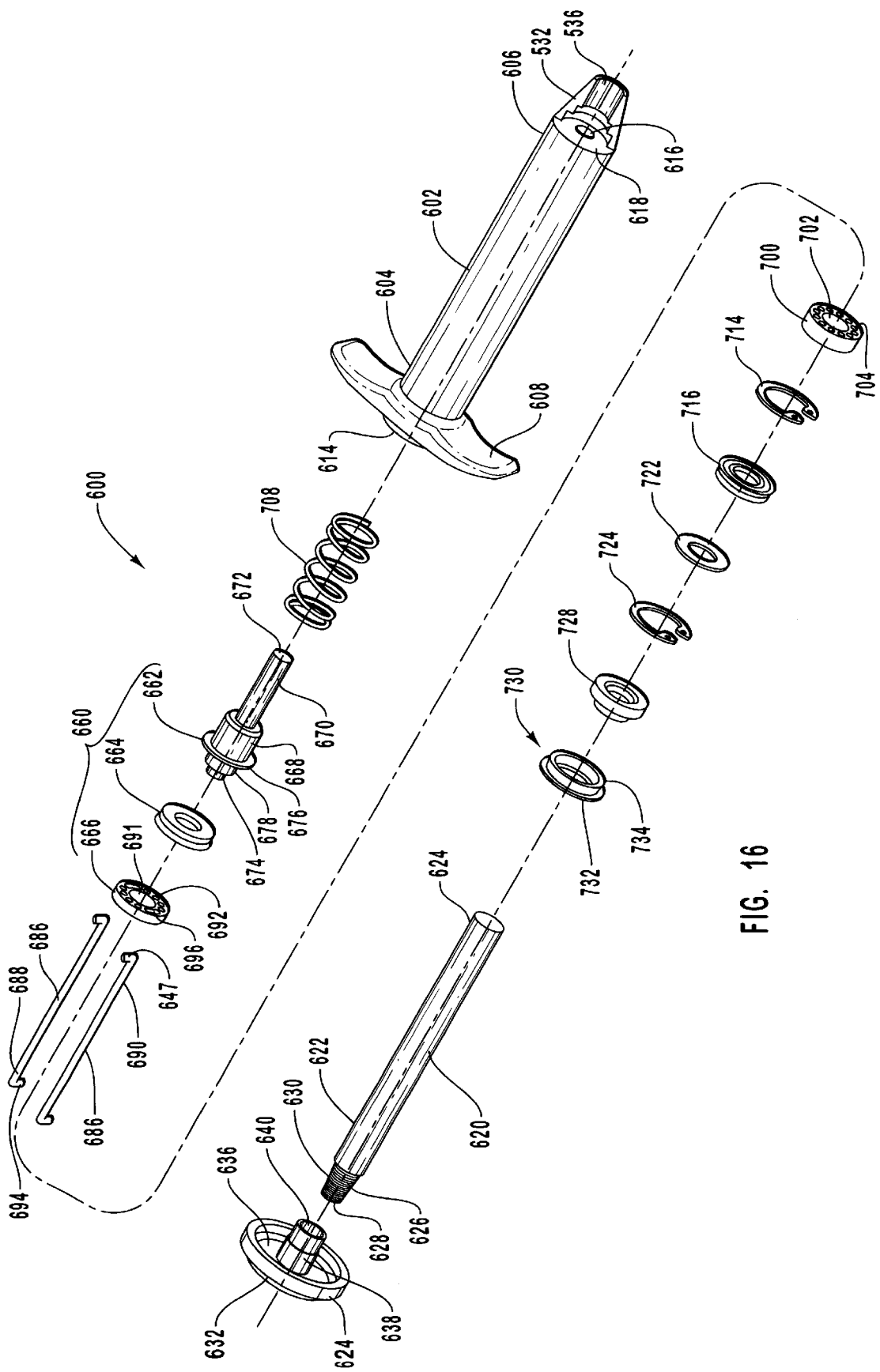
FIG. 16 is a perspective disassembled view of yet another alternative embodiment of a hydraulic syringe.
Figure 17:
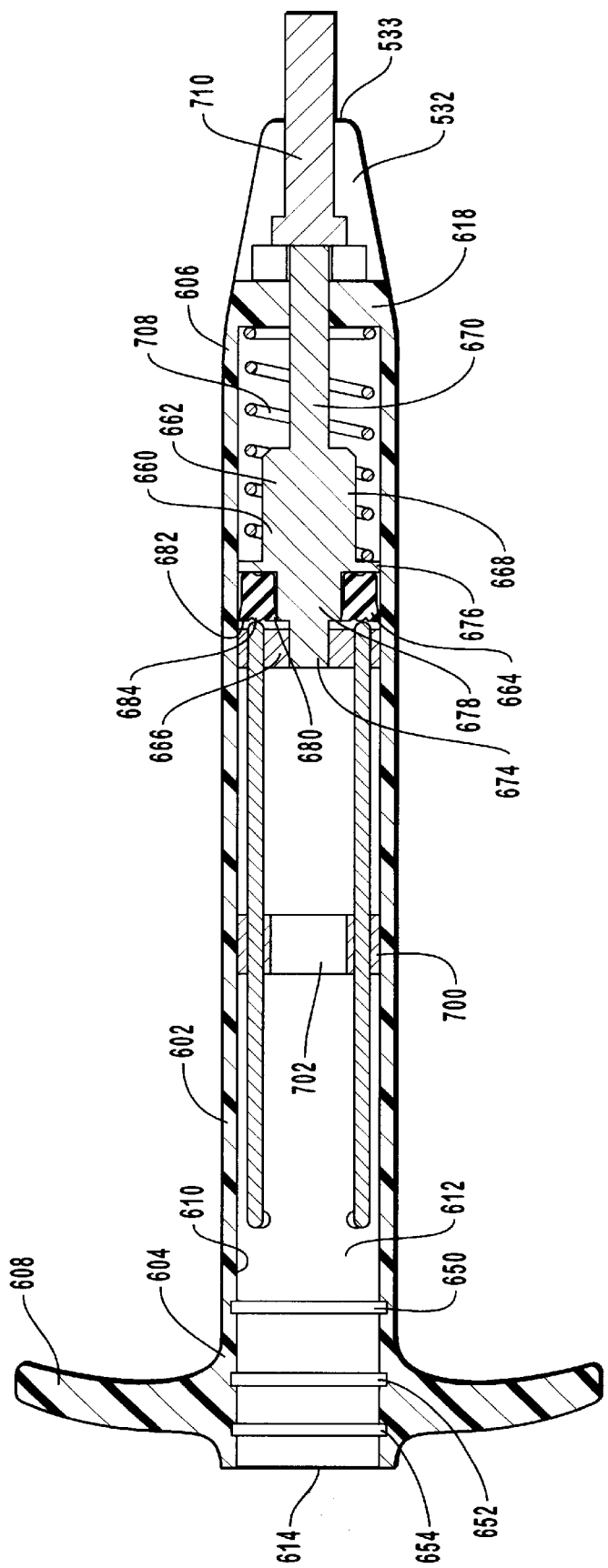
FIG. 17 is a cross sectional side view of the syringe shown in FIG. 16 partially assembled to a first stage.

Depicted in FIGS. 16–19 is a final embodiment of an inventive syringe 600 incorporating features of the present invention. Syringe 600 is described below in terms of structure and method of manufacture. As depicted in FIGS. 16 and 17, syringe 600 includes a barrel 602 extending from a first end 604 to an opposing second end 606. Integrally molded with and radially outwardly projecting from first end 604 of barrel 602 are a pair of opposing finger grips 608. Barrel 602 has an interior surface 610 bounding a chamber 612. Chamber 612 communicates with the exterior through an inlet port 614 positioned at first end 604 and an opposing outlet port 616. Outlet port 616 extends through an end wall 618 positioned at second end 606.

As discussed below in greater detail, an annular first groove 650, an annular second groove 652, and an annular third groove 654 are recessed in spaced apart position on interior surface 610 of barrel 602 at first end 604. Furthermore, an elongated mounting arm 532, as previously discussed with regard to FIGS. 10, 14, and 15, projects from end wall 618 to a free tip 533. With regard to mounting arm 532, like elements between syringe 430 and syringe 600 will be referenced with like reference characters.

Slidably disposed within chamber 612 is a hydraulic plunger 660. Hydraulic plunger 660 includes a piston 662, an annular seal 664, and a nut 666 securing seal 664 to piston 662. Piston 662 includes a substantially cylindrical central body portion 668. An elongated cylindrical shaft 670 projects from body portion 668 to a freely exposed terminus 672. Shaft 670 is slidably disposed within outlet port 616 so as to extend through end wall 618.

Piston 662 also includes a substantially cylindrical attachment post 674, an annular radially outwardly projecting flange 676, and a substantially cylindrical shoulder 678 extending therebetween. Seal 664 radially encircles shoulder 678 so as to bias against flange 676. In the embodiment depicted, seal 664 comprises a loaded lip seal having an inside wing 680 and an outside wing 682 each facing towards first end 604 of barrel 602. In contrast to previously discussed seal 518 which has a separate o-ring 524 disposed between its wings 520 and 522, seal 664 has a central annular ridge 684 that is integrally formed with seal 664 but performs the same function as o-ring 524. In one embodiment, seal 664 is formed from ethylene propylene (EP) but can also be made from a number of different materials. Furthermore, seal 664 can comprise an o-ring or any other type of conventional sealing structure such as those previously discussed.

Nut 666 has a central aperture 691 and a plurality of peripheral holes 692 each extending therethrough. Nut 666 is press fit, screwed on, or otherwise secured to post 674 so as to retain seal 664 between nut 666 and flange 676. In this configuration, outside wing 680 of seal 664 projects slightly past the maximum outer diameter of nut 666 and flange 676.

Syringe 600 also includes a pair of retraction rods 686 each having a first end 688 terminating at a first tip 694 and an opposing second end 690 terminating at a second tip 697. Second end 690 of each retraction rod 686 is secured to nut 666. In the embodiment depicted, second end 690 of each rod 686 is passed through a corresponding peripheral hole 692 in nut 666. Each second tip 697 is then bent over, crimped, flared or otherwise deformed as to prevent each second tip 697 from passing back through corresponding hole 692. An enlarge recess 696 is form on the side of nut 666 so as to receive each second tip 697. In alternative embodiments, rods 686 can be secured to nut 666 such as by threaded engagement, welding, adhesive, or any other convention method.

An annular guide 700 is provided having a central opening 702 extending therethrough and a plurality of peripheral ports 704 extending therethrough. Each retraction rod 686 extends through a corresponding port 704 so that guide 700 can freely slide along the length of retraction rods 686. Each first tip 694 of retractions rods 686 is bent over or otherwise flared or enlarged so as to prevent guide 700 from sliding off first end 688 of retraction rods 686.

During assembly, initially a spring 708 is disposed within chamber 612 of barrel 602 and a plug 710 is manually clipped into channel 536 of mounting arm 532. As discussed below in greater detail, plug 710 is used to limit the passage of shaft 670 through outlet port 616 during assembly of syringe 600.

Next, hydraulic plunger 660 is prepared for insertion into chamber 612. To ensure that seal 664 produces an effective liquid tight seal against interior surface 610 of barrel 602, outside wing 682 is configured having an outer diameter that is slightly larger than the inner diameter of barrel 602. Accordingly, to minimize any potential damage to seal 664 as it is passed over grooves 650, 652, and 654 of barrel 602 during insertion, seal 664, which is mounted to piston 662, can initially be slid within a tubular compression ring (not shown) having an inner diameter the same as the inner diameter of barrel 602. As a result, outside wing 682 is inwardly compressed to the corresponding diameter. Seal 664 is typically retained within the compression ring for more than 9 hours and preferably more than 12 hours so that outside wing 682 relaxes to the diameter of the compression ring. The time to obtain relaxation can be decreased if the seal is heated.

Due to the material properties of seal 664, outside wing 682 substantially retains the relaxed formation for a time period before it begins to outwardly expand. Accordingly, during the time period in which outside wing 682 is in the relaxed formation, hydraulic plunger 660 with retractions rods 686 and guide sleeve 700 are slidably advanced within chamber 612 of barrel 602 past grooves 650, 652, and 654. To further assist the insertion of hydraulic plunger 660 within chamber 612, a hydraulic fluid or other form of lubricant can be applied to interior surface 610 of barrel 602 prior to insertion.

Seal 664 is configured such that once disposed within chamber 612, inside wing 680 biases in sealed engagement against shoulder 678 of piston 662 and outside wing 682 biases in sealed engagement against interior surface 610 of barrel 602.

Next, chamber 612 is filled to a predetermined level with a hydraulic fluid. This is accomplished by dispensing the hydraulic fluid into chamber 612 through inlet port 614. The resulting barrel assembly with hydraulic fluid is then positioned within a vacuum chamber so as to substantially remove all air bubbles that may be contained with the hydraulic fluid or that portion of the assembly covered by the hydraulic fluid. In one embodiment, the barrel assembly is subject to a vacuum in a range from 15 mm Hg to about 30 mm Hg with about 20 mm Hg to about 25 mm Hg being more preferred. The vacuum is typically applied for a period greater than about 2 hours and more preferably greater than about 3 hours.

Figure 18:
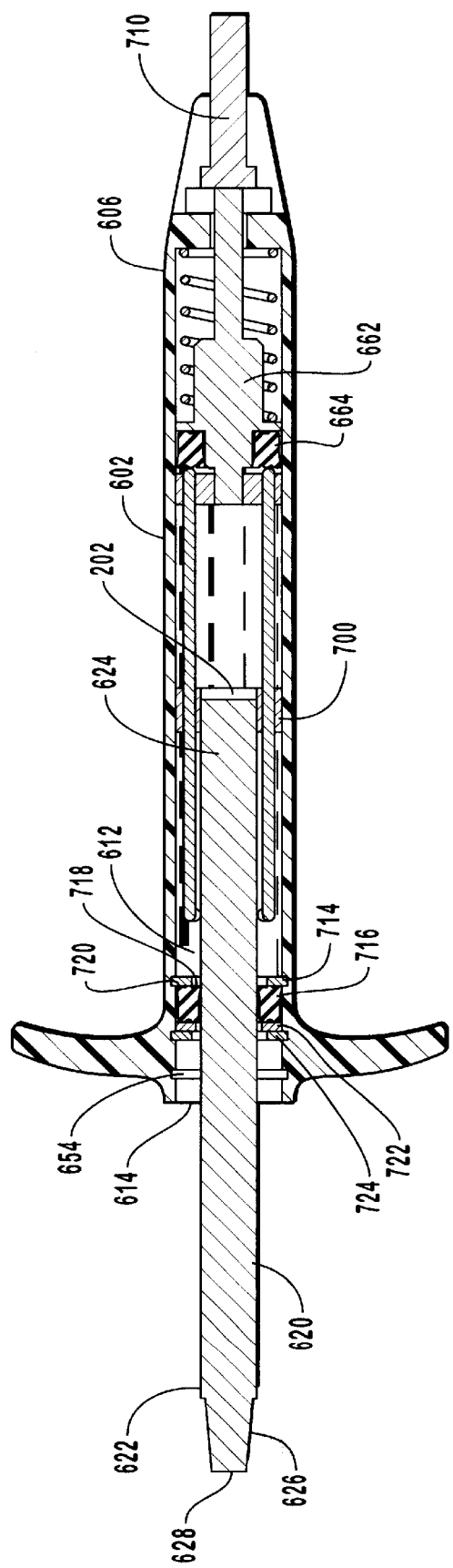
FIG. 18 is a cross sectional side view of the syringe shown in FIG. 16 partially assembled to a second stage.

As depicted in FIGS. 16 and 18, with the air removed, a c-shaped first retaining ring 714 is disposed within first groove 650 by way of inlet port 614. An annular seal 716 is next advanced within chamber 612 so as to bias against first retaining ring 714, ring 714 functioning as a stop. Seal 716 has a configuration substantially identical to seal 664 with an inside wing 718 and an outside wing 720 facing second end 606 of barrel 602. In alternative embodiments, seal 716 can have alternative configurations and compositions as previously discussed. To facilitate insertion of seal 716 over grooves 652 and 654, seal 716 can also be positioned within a compression ring, as discussed above with regard to seal 664, prior to insertion.

A washer 722 is next positioned against seal 716 following which a c-shaped second retaining ring 724 is positioned within second groove 652. Washer 722 functions as a support for seal 716 as pressure is applied thereagainst.

Syringe 600 also includes a manual plunger 620. Manual plunger 620 has a substantially cylindrical shaft-like configuration and extends from a first end 622 to an opposing second end 624. Formed at first end 622 is an tapered post 626 that inwardly slopes in a frustuconical configuration to a terminus 628. A plurality of annular ridges 630 are formed on post 626.

During assembly, second end 624 of manual plunger 620 is centrally passed through washer 722 and seal 716, and then aligned with opening 202 of guide 700. This assembly is disposed within a press (not shown) such that the press applies opposing forces between the bottom of plug 710 and first end 622 of manual plunger 620. The force on the press is increased until second end 624 of manual plunger 620 is press fit within opening 202 of guide 700. The resulting assembly is then removed from the press. In this configuration, inside wing 718 of seal 716 is biased in sealed engagement against manual plunger 620 and outside wing 720 is biased in sealed engagement against interior surface 610 of barrel 602.

Figure 19:
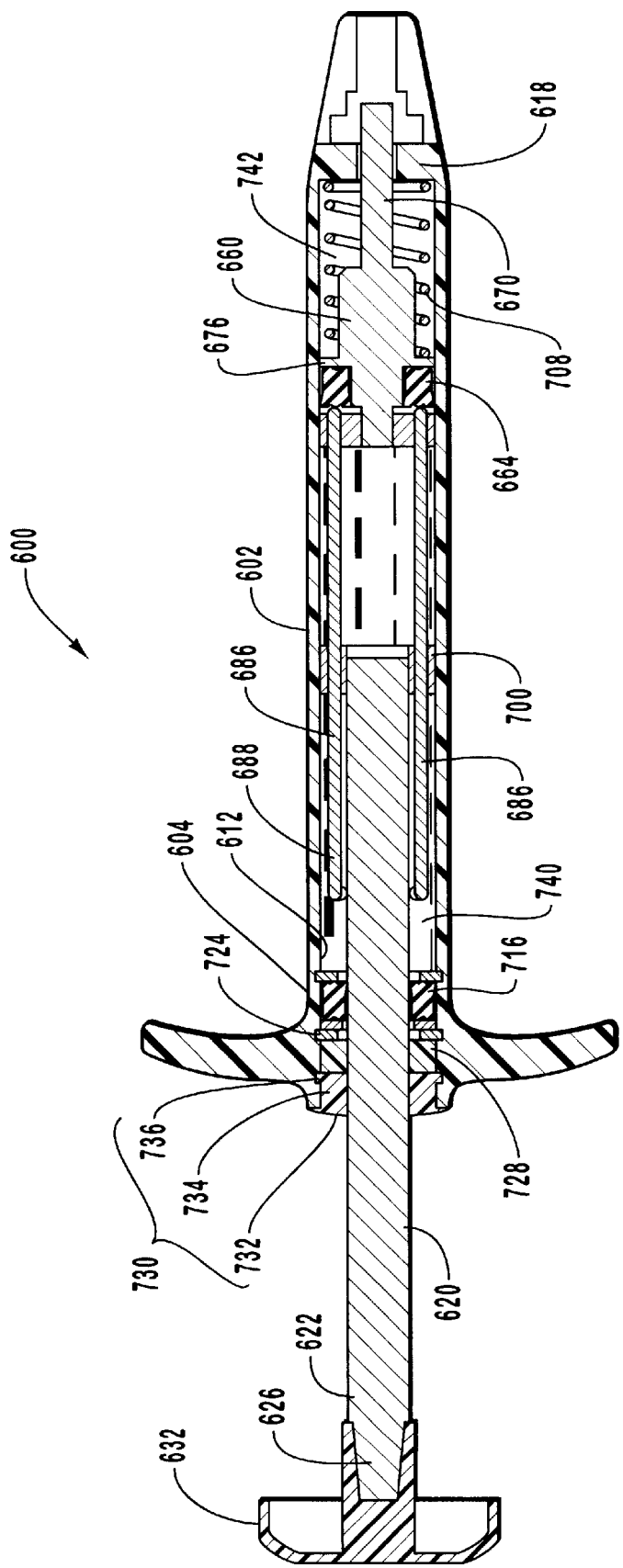
FIG. 19 is a cross sectional side view of the fully assembled syringe shown in FIG. 16.

As depicted in FIGS. 16 and 19, a annular wiper ring 728 is positioned over first end 622 of manual plunger 620 and slidably advanced into chamber 612 so as to bias against second retention ring 724. Wiper ring 728 seals against the side of manual plunger 620 to help prevent the escape of hydraulic fluid from within chamber 612 and prevent the entrance of particulate contaminate from outside of chamber 612. Examples of wiper rings include the D, SHD, and U type wiper rings available from Parker Seals out of Irving, Calif. It is appreciated that in alternative embodiments, wiper ring 728 is not required. In this embodiment, seal 716 independently functions to prevent the escape of hydraulic fluid and the entrance of contaminants.

An end cap 730 has an enlarged head 732 with an annular collar 734 extending therefrom. A annular ridge 736 radially outwardly projects from the free end of collar 734. First end 622 of manual plunger 620 is advanced through an opening 736 extending through end cap 730. End cap 730 is then press fit into inlet port 614 such that ridge 736 locks within third groove 654.

Finally, syringe 600 also includes a handle 632 having an enlarge annular rest 624 with a front face 636. Projecting from front face 636 is a tubular stem 638 bounding an opening 640. Opening 640 is configured substantially complimentary to tapered post 626. Post 626 is manually press fit into opening 640 such that ridges 630 engage post 638, thereby producing a secure frictional engagement. As discussed in other embodiments, there are of course a number of alternative ways in which handle 632 can be secured to manual plunger 620.

During use, manual plunger 620 is withdrawn to a fully retracted position. Plug 710 is removed and replaced with a dispensing cartridge 546 as shown and discussed with regard to FIG. 14. Depicted in FIG. 19, as manual plunger 620 is selectively advanced into chamber 612 of barrel 602, guide 700 travels along retraction rods 686. The hydraulic fluid within chamber 612 passes either around guide 700 or through ports 704 extending therethrough.

Chamber 612 is divided into a first compartment 740 and a second compartment 742. First compartment 740 extends from seal 716 at first end 604 of barrel 602 to seal 664 of hydraulic plunger 660. Second compartment 742 extends from seal 664 to end wall 618. The sizes of first compartment 740 and second compartment 742 vary depending on the position of hydraulic plunger 660 along the length of barrel 602. The hydraulic fluid, as previously discussed, is disposed within first compartment 740. As manual plunger 620 is advanced within first compartment 740, the hydraulic fluid is pressurized which in turn causes hydraulic plunger 660 to advance within barrel 602. Air within second compartment 742 escapes through a gap formed between shaft 670 and outlet port 616.

Manual plunger 620 has an a transverse cross sectional area that is smaller than the transverse cross sectional area extending through seal 664 of hydraulic plunger 660. Accordingly, for substantially the same reasons as previously discussed with regard to the hydraulic syringes 240, 290, 360,380, and 430, as manual plunger 620 is advanced within first compartment 740 under a manual first force at a first speed, hydraulic plunger 660 is advanced under a hydraulic second force greater than the first force and at a second speed slower than the first speed. In turn, the second force is used by shaft 670 of hydraulic plunger 660 to dispense the material from cartridge 546 as previously discussed.

Once the material is dispensed from cartridge 546, manual plunger 620 is manually retracted by pulling on handle 632. As manual plunger 620 is retracted, guide 700 slides along retraction rods 686. Once guide 700 reaches first ends 688 of retraction rods 686, bent first tip portions 694 hold guide 700 to rods 686. Accordingly, as manual plunger 620 is further retracted, retraction rods 686 and attached hydraulic plunger 660 are also manually retracted within chamber 612 of barrel 602. Spring 708 which is biased between end wall 618 and flange 676 of hydraulic plunger 660 also assists in the retraction of hydraulic plunger 660.

In one embodiment of the present invention, means are provided for mechanically retracting hydraulic plunger 660 within chamber 612 of barrel 602 by retracting manual plunge 620. One example of such means comprises the use of retention rods 686 in conjunction with guide 700 as discussed above. In alternative embodiments, the means can comprise a coiled spring; a flexible line such as wire, ribbon, or cord; or any other structure or assembly that can extend between manual plunger 620 and hydraulic plunger 660. Such alternatives should be configured to permit substantially free advancement of manual plunger 620 relative to hydraulic plunger 660 while enabling manual plunger 620 to physically retract hydraulic plunger 660 as manual plunger 620 is retracted.

The present invention may be embodied in other specific forms without departing from its spirit or essential characteristics. The described embodiments are to be considered in all respects only as illustrative and not restrictive. For example, the different components and elements of the of the various described syringes can be combined and mixed into different configurations. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A syringe comprising:
   a syringe barrel having an interior surface bounding a chamber, the chamber extending from a first end to an opposing second end;
   a manual plunger coupled with the syringe barrel so as to selectively advance within the first end of the chamber;
   at least a portion of a hydraulic plunger slidably disposed within the second end of the chamber, the hydraulic plunger including:
   a piston body; and
   a shaft projecting from the piston body, the shaft selectively extending through an opening formed at the second end of the chamber; and
   a first seal coupled with the piston body and producing a liquid tight seal with the interior surface of the syringe barrel;
   a hydraulic fluid sealably disposed within the chamber of the syringe barrel, at least a portion of the hydraulic fluid being disposed between the manual plunger and the hydraulic plunger such that as the manual plunger is selectively advanced within the chamber, the hydraulic fluid advances the hydraulic plunger within the chamber; and
   means operably connected to the manual plunger for mechanically retracting the hydraulic plunger when the manual plunger is retracted.

2. A syringe as recited in claim 1, wherein the chamber has a substantially uniform transverse cross section along the length of the syringe barrel.

3. A syringe as recited in claim 1, wherein the first seal comprises a loaded lip seal having an annular inside wing and an annular outside wing.

4. A syringe as recited in claim 1, wherein the means for retracting the hydraulic plunger comprises:
   a rod operably connected to the piston body, the rod projecting from the piston body in a direction opposite from the shaft; and
   a guide secured to the manual plunger, the rod extending through a portion of the guide such that the guide can selectively advance along at least a portion of the rod.

5. A syringe as recited in claim 1, wherein the means for retracting comprises a rod attached to and projecting from the hydraulic plunger toward the first end of the chamber, at least a portion of the rod being disposed within the chamber of the barrel, the manual plunger being secured to the rod such that the manual plunger can freely advance within the chamber without mechanically advancing the rod and the manual plunger can be retracted within the chamber so as to mechanically retract within the chamber the rod and the hydraulic plunger attached thereto.

6. A syringe as recited in claim 1, further comprising a spring disposed within the second end of the chamber of the syringe barrel such that the spring can be selectively compressed between at least a portion of the hydraulic plunger and the second end of the syringe barrel.

7. A syringe as recited in claim 1, further comprising:
   the hydraulic plunger having a shaft selectively projecting through an opening formed at the second end of the syringe barrel; and
   a mounting arm projecting at the second end of the syringe barrel, the mounting arm having an inside surface bounding an exposed substantially U-shaped channel extending along at least a portion of the length thereof, the channel being configured to receive the shaft of the hydraulic plunger.

8. A syringe as recited in claim 7, further comprising a cartridge having a barrel with an inlet end and an opposing outlet end, the cartridge being configured to be removably disposed within the channel of the mounting arm so as to selectively receive the shaft of the hydraulic plunger.

9. A syringe as recited in claim 7, further comprising a second seal secured within the chamber of the syringe barrel at the first end thereof, the second seal producing a liquid tight seal between the interior surface of the syringe barrel and the manual plunger.

10. A syringe as recited in claim 9, further comprising a support ring disposed against the second seal on the side opposite the hydraulic plunger.

11. A syringe as recited in claim 9, further comprising a wiper ring disposed within the chamber of the syringe barrel, the wiper ring encircling the manual plunger.

12. A syringe as recited in claim 1, wherein the transverse cross sectional area of the manual plunger is smaller than the maximum transverse cross sectional area of the hydraulic plunger.

13. A syringe as recited in claim 1, wherein the hydraulic fluid has a viscosity in a range between about 500 centistoke to about 5,000 centistoke.

14. A syringe comprising:
   a syringe barrel having an interior surface bounding a chamber, the chamber extending from a first end to an opposing second end;
   a manual plunger coupled with the syringe barrel so as to selectively advance within the first end of the chamber;
   a hydraulic plunger slidably disposed within the second end of the chamber, the hydraulic plunger having a shaft selectively extending through an opening formed at the second end of the barrel, the hydraulic plunger including:
      a piston body; and
      a shaft projecting from the piston body, the shaft selectively extending through an opening formed at the second end of the chamber; and
      a first seal coupled with the piston body and producing a liquid tight seal with the interior surface of the syringe barrel;
   a hydraulic fluid sealably disposed within the chamber of the syringe barrel, at least a portion of the hydraulic fluid being disposed between the manual plunger and the hydraulic plunger such that as the manual plunger is selectively advanced within the chamber, the hydraulic fluid advances the hydraulic plunger within the chamber;
   a rod extending between the manual plunger and the hydraulic plunger, the rod operably connected to the piston body, the rod projecting from the piston body in a direction opposite from the shaft; and
   a guide secured to the manual plunger, the rod extending through a portion of the guide such that the guide can selectively advance along at least a portion of the rod.

15. A syringe as recited in claim 14, wherein the guide includes a passageway extending therethrough, and wherein the rod includes a first end and an opposing second end, the second end of the rod being secured to the piston body such that the rod projects toward the first end of the barrel, the rod extending through the passageway of the guide such that the guide can selectively slide along the length of the rod, the first end of the rod being configured to prevent the guide from sliding off of the rod.

16. A syringe as recited in claim 14, further comprising a spring disposed within the second end of the chamber of the syringe barrel such that the spring can be selectively compressed between at least a portion of the hydraulic plunger and the second end of the syringe barrel.

17. A syringe as recited in claim 14, further comprising a mounting arm projecting at the second end of the syringe barrel, the mounting arm having an inside surface bounding an exposed substantially U-shaped channel extending along at least a portion of the length thereof, the channel being configured to receive the shaft of the hydraulic plunger.

18. A syringe as recited in claim 17, further comprising a cartridge having a barrel with an inlet end and an opposing outlet end, the cartridge being configured to be removably disposed within the channel of the mounting arm so as to selectively receive the shaft of the hydraulic plunger.

19. A syringe as recited in claim 14, further comprising a seal secured within the chamber of the syringe barrel at the first end thereof, the seal encircling the manual plunger producing a liquid tight seal between the interior surface of the syringe barrel and the manual plunger.

20. A syringe as recited in claim 19, further comprising a support ring disposed against the seal on the side opposite the hydraulic plunger.

21. A syringe as recited in claim 19, further comprising a wiper ring disposed within the chamber of the syringe barrel, the wiper ring encircling the manual plunger.

22. A syringe comprising:
   a syringe barrel having an interior surface bounding a chamber, the chamber extending from a first end to an opposing second end;
   a manual plunger having a first end and an opposing second end, the second end of the manual plunger being slidably disposed within the first end of the chamber of the syringe barrel;
   a guide secured to and radially outwardly projecting from the second end of the manual plunger;
   a first seal disposed within the first end of the chamber of the syringe barrel, the first seal encircling the manual plunger so as to effect a liquid tight seal between the syringe barrel and the manual plunger;
   a piston including:
      an enlarged body slidably disposed within the second end of the chamber of the syringe barrel; and
      a shaft projecting from the body through the second end of the syringe barrel;
   a second seal mounted to the piston within the second end of the chamber of the syringe barrel, the second seal encircling the piston so as to effect a liquid tight seal between the piston and the syringe barrel;
   a hydraulic fluid sealed within the chamber of the syringe barrel between the first seal and the second seal, such that as the manual plunger is selectively advanced within the chamber, the hydraulic fluid advances the hydraulic plunger within the chamber; and
   a rod operably connected to the piston, the rod projecting toward the first end of the chamber, the rod extending through a portion of the guide such that the guide can advance relative to the rod, and such that the manual plunger is enabled to retract the hydraulic plunger with the guide and the rod.

23. A syringe as recited in claim 22, wherein at least one of the first seal and second seal comprises a loaded lip seal having an annular inside wing and an annular outside wing.

24. A syringe as recited in claim 22, her comprising:
   a mounting arm positioned at the second end of the syringe barrel, the mounting arm having an inside surface bounding an exposed substantially U-shaped channel extending along the length thereof, the channel being configured to receive the shaft of the piston as the piston is advanced within chamber of the syringe barrel; and
   a cartridge comprising a barrel having an inlet end and an opposing outlet end, the cartridge being configured to be removably disposed within the channel of the mounting arm.

25. A syringe as recited in claim 22, further comprising a spring disposed between at least a portion of the piston and the second end of the barrel.

26. A method for manufacturing a hydraulic syringe comprising:
   positioning at least a portion of a hydraulic plunger within a chamber of a syringe barrel, the chamber extending from a first end to an opposing second end, the hydraulic plunger being slidably positioned within the chamber such that a shaft of the hydraulic plunger selectively projects through an opening formed at the second end of the barrel;
   dispensing a hydraulic fluid within the chamber of the syringe barrel between the hydraulic plunger and the first end of the chamber;
   connecting a rod to the hydraulic plunger, the rod projecting from the hydraulic plunger in a direction opposite of the shaft;
   slidably securing a guide to the rod such that the guide can slide along the length of the rod;
   inserting a manual plunger within the first end of the chamber of the syringe barrel, the manual plunger being configured relative to the hydraulic plunger such that as the manual plunger is advanced within the chamber under a first force, the hydraulic plunger is advanced by the hydraulic fluid under a second force, the second force being greater than the first force; and
   connecting the manual plunger with the guide, such that the guide and the rod interconnect the manual plunger and the hydraulic plunger, such that the manual plunger is enabled to retract the hydraulic plunger with the guide and the rod.

27. A method as recited in claim 26, further comprising inserting a spring within the chamber of the syringe barrel prior to positioning of the hydraulic plunger, the spring being selectively compressed between the hydraulic plunger and the second end of the syringe barrel.

28. A method as recited in claim 26, wherein each of the hydraulic plunger and the manual plunger comprises an annular seal for producing a liquid tight seal against the interior surface of the syringe barrel, such that the hydraulic fluid is sealed within the chamber of the syringe barrel between the annular seals.

29. A method as recited in claim 26, further comprising applying a relative vacuum to the hydraulic fluid within the syringe barrel so as to substantially remove trapped gasses therefrom.

30. A method as recited in claim 26, further comprising removably securing a dispensing cartridge to the second end of the syringe barrel, the dispensing cartridge being configured to receive the shaft of the hydraulic plunger.

* * * * *

UNITED STATES PATENT AND TRADEMARK OFFICE
CERTIFICATE OF CORRECTION

PATENT NO. : 6,527,751 B2
DATED : March 4, 2003
INVENTOR(S) : Fischer et al.

It is certified that error appears in the above-identified patent and that said Letters Patent is hereby corrected as shown below:

Column 3,
Line 33, after "FIG. 14 is" please insert -- a --
Line 65, before "uses, such as" please change "non-medial" to -- non-medical --

Column 9,
Line 51, after "extends between" please change "an" to -- a --

Column 14,
Line 24, after "1º to about" please change "100" to -- 10º --
Line 52, after "502 by" please change "used" to -- use --

Column 15,
Line 42, before "annular flange" please change "a" to -- an --
Line 62, after "4,384,853;" please change "4,4,767,326;" to -- 4,767,326 --

Column 18,
Line 11, after "first end 622 is" please change "an" to -- a --
Line 28, after "FIGS. 16 and 19," please change "a" to -- an --
Line 42, after "extending therefrom." please change "A" to -- An --

Column 19,
Line 13, after "plunger 620 has" please remove "an"

Column 22,
Line 58, after "in claim 22," please remove "her" and insert -- further --

Signed and Sealed this

Twenty-seventh Day of January, 2004

JON W. DUDAS
*Acting Director of the United States Patent and Trademark Office*